US010989708B2

(12) United States Patent
Yabutani et al.

(10) Patent No.: US 10,989,708 B2
(45) Date of Patent: Apr. 27, 2021

(54) AUTOMATED ANALYSIS DEVICE

(71) Applicant: Hitachi High-Technologies Corporation, Tokyo (JP)

(72) Inventors: Chie Yabutani, Tokyo (JP); Sumiko Murata, Tokyo (JP); Akihisa Makino, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 378 days.

(21) Appl. No.: 16/076,340

(22) PCT Filed: Mar. 1, 2017

(86) PCT No.: PCT/JP2017/008046
§ 371 (c)(1),
(2) Date: Aug. 8, 2018

(87) PCT Pub. No.: WO2017/159359
PCT Pub. Date: Sep. 21, 2017

(65) Prior Publication Data
US 2019/0041386 A1 Feb. 7, 2019

(30) Foreign Application Priority Data

Mar. 16, 2016 (JP) .............................. JP2016-051814

(51) Int. Cl.
*G01N 33/53* (2006.01)
*G01N 35/04* (2006.01)
(Continued)

(52) U.S. Cl.
CPC ......... *G01N 33/5304* (2013.01); *G01N 33/86* (2013.01); *G01N 35/02* (2013.01);
(Continued)

(58) Field of Classification Search
None
See application file for complete search history.

(56) References Cited

U.S. PATENT DOCUMENTS

2012/0160039 A1* 6/2012 Tatsutani ............. G01N 1/2813
73/863.91
2015/0104351 A1 4/2015 Makino et al.

FOREIGN PATENT DOCUMENTS

EP 0 488 247 A2 6/1992
EP 1 975 630 A2 10/2008
(Continued)

OTHER PUBLICATIONS

International Search Report of PCT/JP2017/008046 dated Jun. 24, 2017.
(Continued)

*Primary Examiner* — Kathryn Wright
(74) *Attorney, Agent, or Firm* — Mattingly & Malur, PC

(57) ABSTRACT

An automated analysis device includes: a first measurement unit having a reaction disc for retaining a plurality of reaction cells containing a mixed solution of sample and reagent on a circumference, a light source for irradiating the mixed solution contained in the reaction cells with light, and a light-receiving unit for detecting the irradiated light; a cleaning mechanism for cleaning the reaction cells having undergone measurement; disposable reaction containers for containing the mixed solution of sample and reagent; a second measurement unit that has a plurality of measurement channels for retaining the disposable reaction containers, and includes a light source for irradiating the disposable reaction containers retained in each of the plurality of measurement channels with light; a read unit for reading identification information; and a control unit for controlling an analysis condition for the sample on the basis of the information that has been read.

16 Claims, 21 Drawing Sheets

(51) Int. Cl.
  *G01N 35/10* (2006.01)
  *G01N 35/02* (2006.01)
  *G01N 33/86* (2006.01)
(52) U.S. Cl.
  CPC ......... *G01N 35/04* (2013.01); *G01N 35/1002* (2013.01); *G01N 2035/0437* (2013.01); *G01N 2035/0441* (2013.01); *G01N 2035/0443* (2013.01); *G01N 2035/0453* (2013.01)

(56) References Cited

FOREIGN PATENT DOCUMENTS

| | | | |
|---|---|---|---|
| EP | 2 485 054 A1 | 8/2012 | |
| EP | 3 144 678 A1 | 3/2017 | |
| JP | 04-256855 A | 9/1992 | |
| JP | 04-329359 A | 11/1992 | |
| JP | 06-051870 U | 7/1994 | |
| JP | 07-049346 A | 2/1995 | |
| JP | 2007-057321 A | 3/2007 | |
| JP | 2010181197 A * | 8/2010 | ....... G01N 35/00732 |
| JP | 2011-047920 A | 3/2011 | |
| JP | 2011-209004 A | 10/2011 | |
| WO | 2013/187210 A1 | 12/2013 | |

OTHER PUBLICATIONS

Extended European Search Report received in corresponding European Application No. 17766362.2 dated Nov. 11, 2019.

* cited by examiner

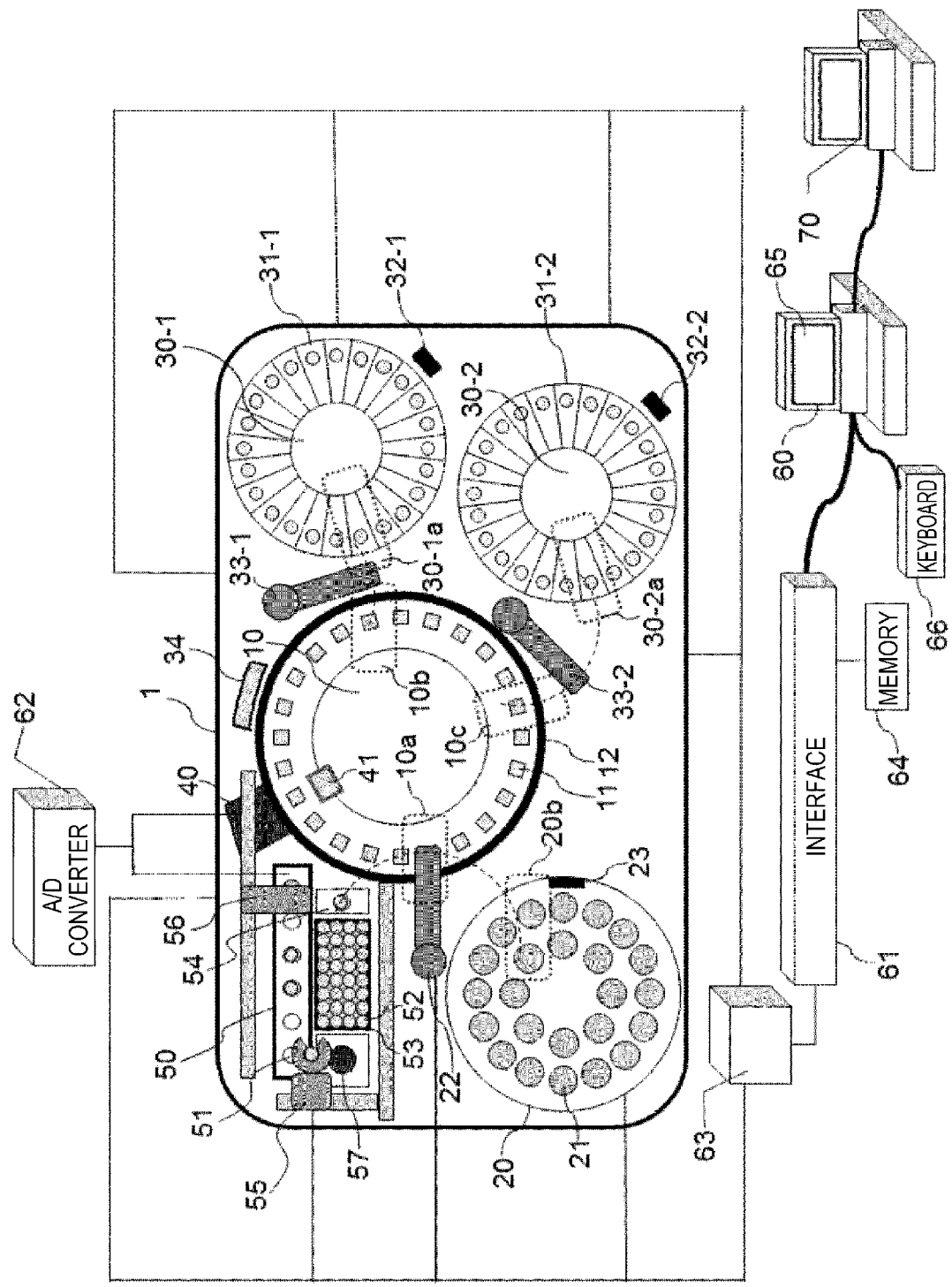
[Fig. 1]

[Fig. 2]
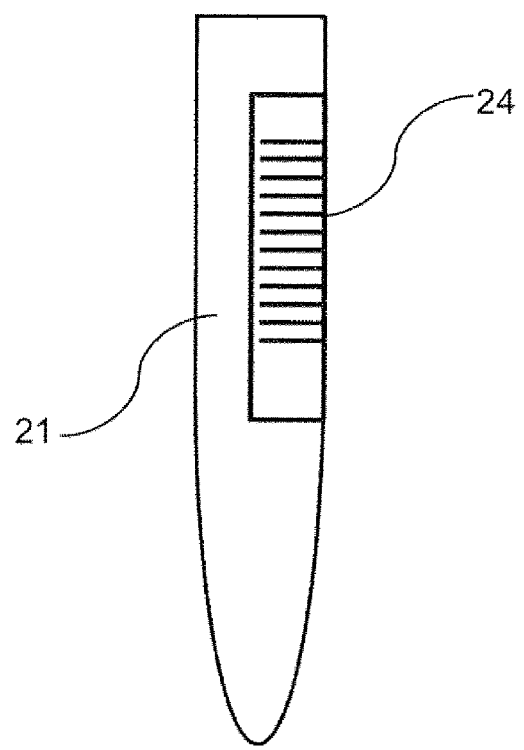

[Fig. 3]
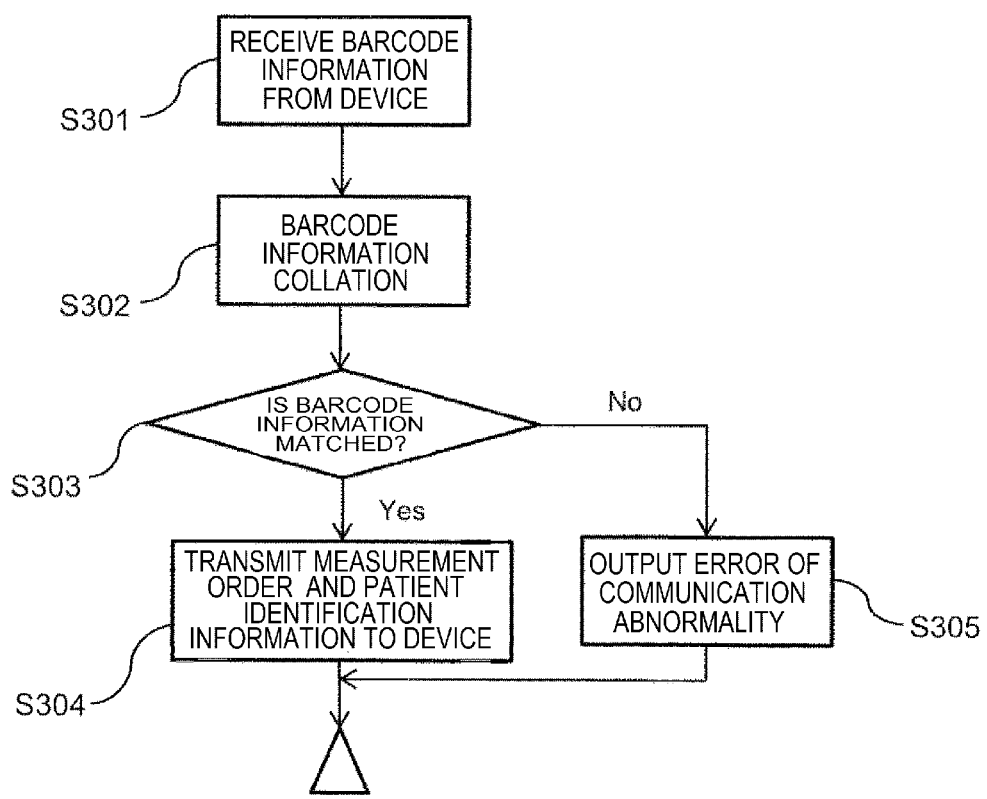

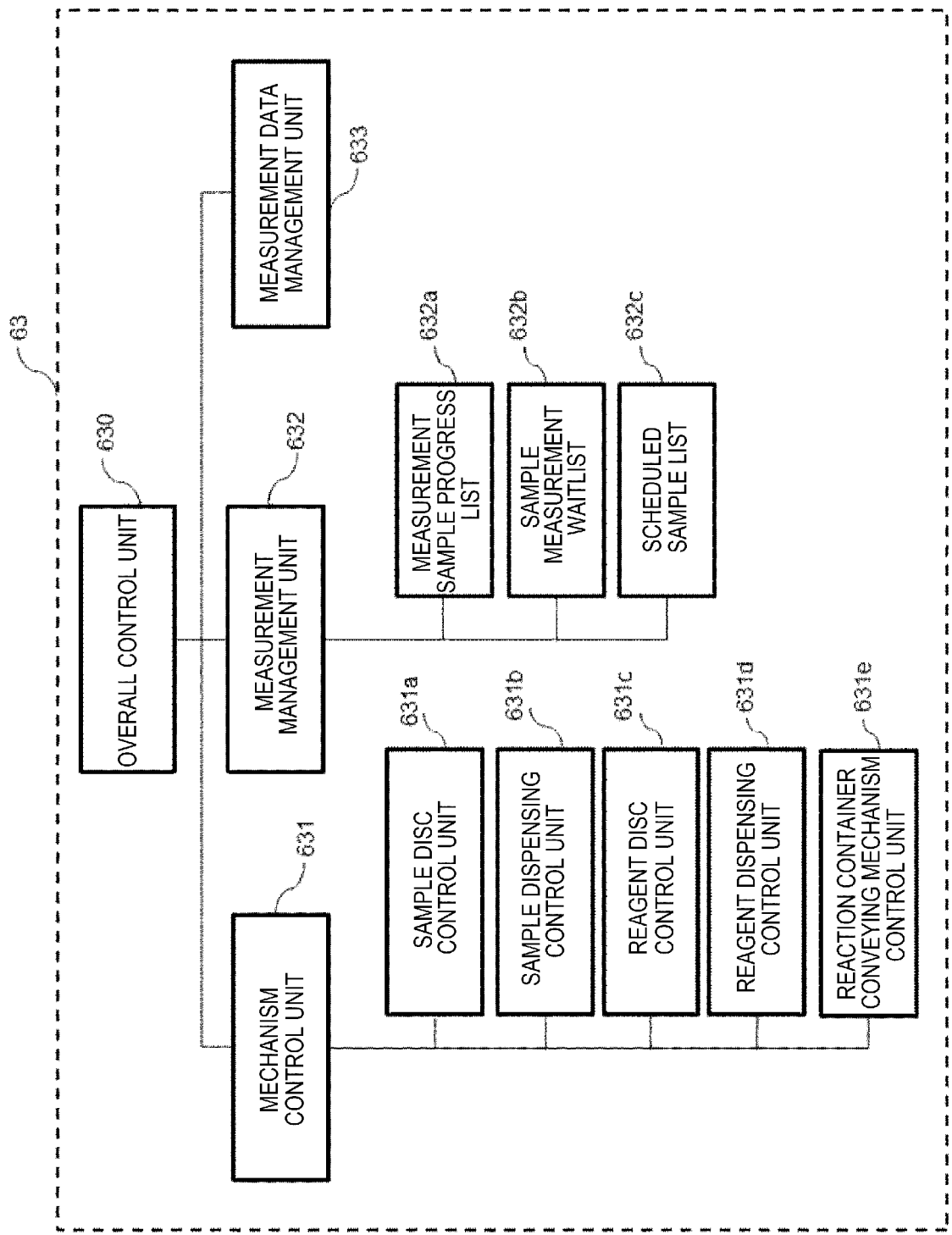
[Fig. 4]

[Fig. 5]
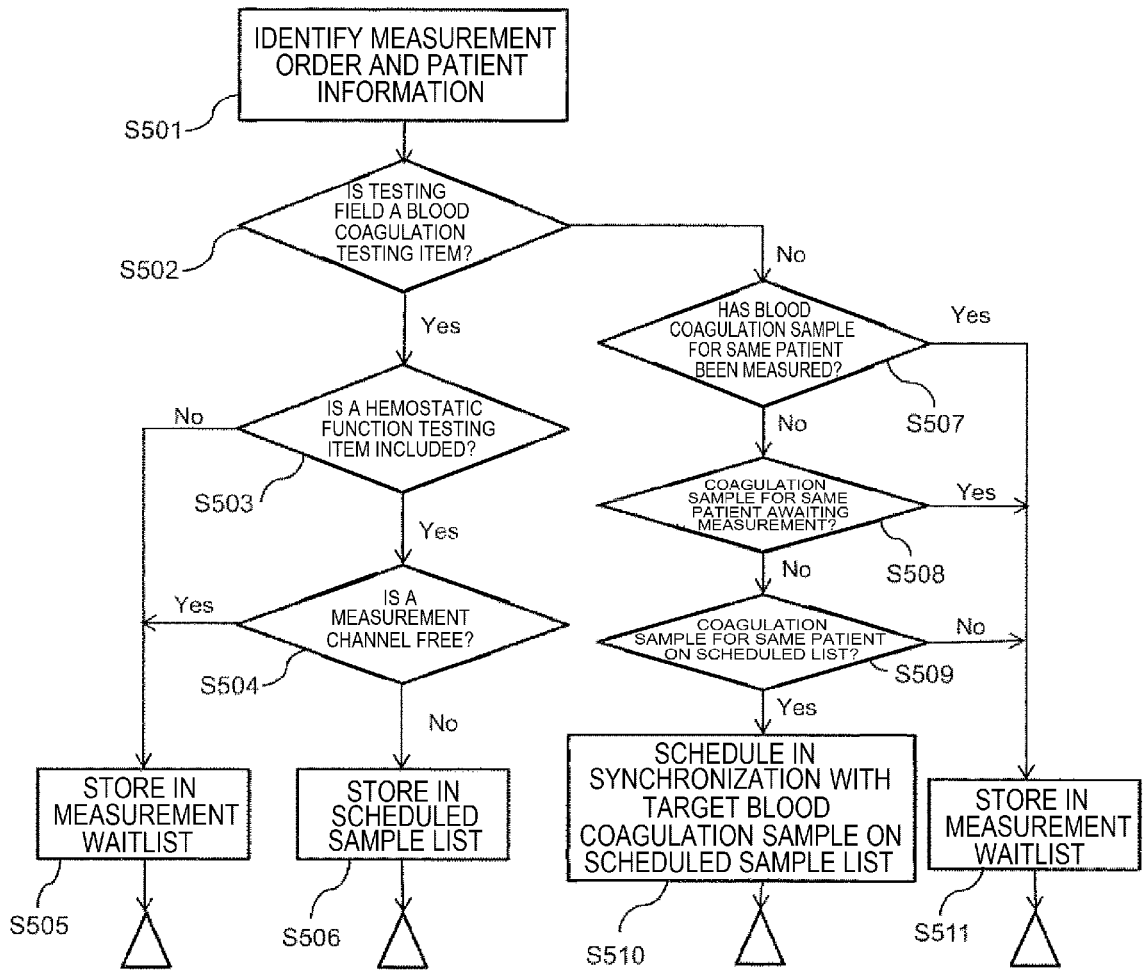

[Fig. 6]
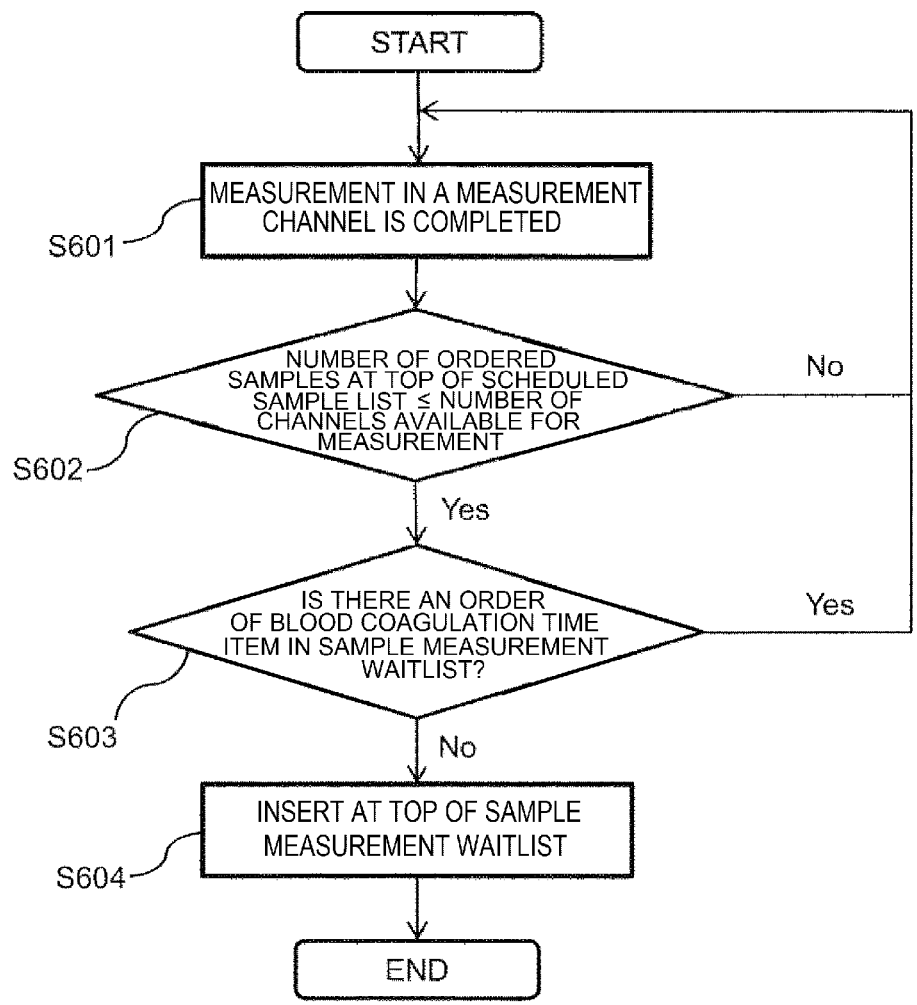

[Fig. 7A]

MEASUREMENT SAMPLE PROGRESS LIST 701

| S. No | MEASUREMENT STATUS | PATIENT ID | TESTING FIELD | PHOTOMETER ORDER NUMBER | BLOOD COAGULATION TIME MEASUREMENT UNIT ORDER NUMBER |
|---|---|---|---|---|---|
| 1 |  | 00001 | BLOOD COAGULATION | 0 | 3 |
| 2 |  | 00003 | BLOOD COAGULATION | 0 | 3 |
| 3 |  | 00005 | BLOOD COAGULATION | 0 | 3 |
| 4 |  | 00006 | BLOOD COAGULATION | 0 | 3 |
| 5 |  | 00010 | BLOOD COAGULATION | 0 | 3 |
| 6 |  | 00001 | BIOCHEMICAL | 18 | 0 |
| 7 |  | 00002 | BIOCHEMICAL | 18 | 0 |
| 8 |  | 00003 | BIOCHEMICAL | 18 | 0 |
| 9 |  | 00004 | BIOCHEMICAL | 18 | 0 |
| 10 |  | 00005 | BIOCHEMICAL | 18 | 0 |
| 11 |  | 00007 | BIOCHEMICAL | 18 | 0 |
| 12 |  | 00008 | BIOCHEMICAL | 18 | 0 |
| 13 |  | 00009 | BIOCHEMICAL | 18 | 0 |
| 14 |  | 00010 | BIOCHEMICAL | 18 | 0 |
| 15 |  | 00011 | BIOCHEMICAL | 18 | 0 |
| 16 |  | 00012 | BIOCHEMICAL | 18 | 0 |
| 17 |  | 00013 | BIOCHEMICAL | 18 | 0 |
| 18 |  | 00014 | BIOCHEMICAL | 18 | 0 |
| 19 |  | 00015 | BIOCHEMICAL | 18 | 0 |
| 20 |  | 00016 | BIOCHEMICAL | 18 | 0 |

[Fig. 7B]

| S. No | MEASUREMENT SAMPLE PROGRESS LIST | | | | | SAMPLE MEASUREMENT WAITLIST | | | SCHEDULED SAMPLE LIST |
|---|---|---|---|---|---|---|---|---|---|
| | MEASUREMENT STATUS | PATIENT ID | TESTING FIELD | PHOTOMETER ORDER NUMBER | BLOOD COAGULATION TIME MEASUREMENT UNIT ORDER NUMBER | MEASUREMENT SEQUENCE | PHOTOMETER | BLOOD COAGULATION TIME MEASUREMENT UNIT | SCHEDULED STATUS |
| 1 | BEING ANALYZED | 00001 | BLOOD COAGULATION | 0 | 3 | 1 | — | 10:00:00 | |
| 2 | BEING ANALYZED | 00003 | BLOOD COAGULATION | 0 | 3 | 2 | — | 10:00:30 | |
| 3 | RECEIVED | 00005 | BLOOD COAGULATION | 0 | 3 | NOT DETERMINED | — | — | SCHEDULED 1 |
| 4 | RECEIVED | 00006 | BLOOD COAGULATION | 0 | 3 | NOT DETERMINED | — | — | SCHEDULED 2 |
| 5 | RECEIVED | 00010 | BLOOD COAGULATION | 0 | 3 | NOT DETERMINED | — | — | SCHEDULED 3 |
| 6 | BEING ANALYZED | 00001 | BIOCHEMICAL | 18 | 0 | 3 | 10:08:30 | — | |
| 7 | | 00002 | BIOCHEMICAL | 18 | 0 | | | | |
| 8 | | 00003 | BIOCHEMICAL | 18 | 0 | | | | |
| 9 | | 00004 | BIOCHEMICAL | 18 | 0 | | | | |
| 10 | | 00005 | BIOCHEMICAL | 18 | 0 | | | | |
| 11 | | 00007 | BIOCHEMICAL | 18 | 0 | | | | |
| 12 | | 00008 | BIOCHEMICAL | 18 | 0 | | | | |
| 13 | | 00009 | BIOCHEMICAL | 18 | 0 | | | | |
| 14 | | 00010 | BIOCHEMICAL | 18 | 0 | | | | |
| 15 | | 00011 | BIOCHEMICAL | 18 | 0 | | | | |
| 16 | | 00012 | BIOCHEMICAL | 18 | 0 | | | | |
| 17 | | 00013 | BIOCHEMICAL | 18 | 0 | | | | |
| 18 | | 00014 | BIOCHEMICAL | 18 | 0 | | | | |
| 19 | | 00015 | BIOCHEMICAL | 18 | 0 | | | | |
| 20 | | 00016 | BIOCHEMICAL | 18 | 0 | | | | |

MEASUREMENT SAMPLE WAITLIST 703

| S.No | MEASUREMENT SAMPLE PROGRESS LIST ||||| SAMPLE MEASUREMENT WAITLIST |||| SCHEDULED SAMPLE LIST ||
|---|---|---|---|---|---|---|---|---|---|---|---|
| | MEASUREMENT STATUS | PATIENT ID | TESTING FIELD | PHOTOMETER ORDER NUMBER | BLOOD COAGULATION TIME MEASUREMENT UNIT ORDER NUMBER | MEASUREMENT SEQUENCE | PHOTOMETER | BLOOD COAGULATION TIME MEASUREMENT UNIT | SCHEDULED STATUS | MEASUREMENT STARTING TIME DIFFERENCE |
| 1 | MEASURED | 00001 | BLOOD COAGULATION | 0 | 3 | 1 | — | 10:00:00 | | |
| 2 | MEASURED | 00003 | BLOOD COAGULATION | 0 | 3 | 2 | — | 10:00:30 | | |
| 3 | MEASURED | 00005 | BLOOD COAGULATION | 0 | 3 | 5 | — | 10:07:00 | | |
| 4 | MEASURED | 00006 | BLOOD COAGULATION | 0 | 3 | 6 | — | 10:07:30 | | |
| 5 | MEASURED | 00010 | BLOOD COAGULATION | 0 | 3 | 9 | — | 10:14:00 | | |
| 6 | MEASURED | 00001 | BIOCHEMICAL | 18 | 0 | 3 | 10:01:00 | — | | 0:01:00 |
| 7 | MEASURED | 00002 | BIOCHEMICAL | 18 | 0 | 4 | 10:04:00 | — | | |
| 8 | MEASURED | 00003 | BIOCHEMICAL | 18 | 0 | 7 | 10:08:00 | — | | 0:07:30 |
| 9 | MEASURED | 00004 | BIOCHEMICAL | 18 | 0 | 8 | 10:11:00 | — | | |
| 10 | MEASURED | 00005 | BIOCHEMICAL | 18 | 0 | 10 | 10:14:30 | — | | 0:07:30 |
| 11 | MEASURED | 00007 | BIOCHEMICAL | 18 | 0 | 11 | 10:17:30 | — | | |
| 12 | MEASURED | 00008 | BIOCHEMICAL | 18 | 0 | 12 | 10:20:30 | — | | |
| 13 | MEASURED | 00009 | BIOCHEMICAL | 18 | 0 | 13 | 10:23:30 | — | | |
| 14 | MEASURED | 00010 | BIOCHEMICAL | 18 | 0 | 14 | 10:26:30 | — | | 0:12:30 |
| 15 | MEASURED | 00011 | BIOCHEMICAL | 18 | 0 | 15 | 10:29:30 | — | | |
| 16 | MEASURED | 00012 | BIOCHEMICAL | 18 | 0 | 16 | 10:32:30 | — | | |
| 17 | MEASURED | 00013 | BIOCHEMICAL | 18 | 0 | 17 | 10:35:30 | — | | |
| 18 | MEASURED | 00014 | BIOCHEMICAL | 18 | 0 | 18 | 10:38:30 | — | | |
| 19 | MEASURED | 00015 | BIOCHEMICAL | 18 | 0 | 19 | 10:41:30 | — | | |
| 20 | MEASURED | 00016 | BIOCHEMICAL | 18 | 0 | 20 | 10:44:30 | — | | |

[Fig. 7D]

| | MEASUREMENT SAMPLE PROGRESS LIST | | | | | SAMPLE MEASUREMENT WAITLIST | | | SCHEDULED SAMPLE LIST | |
|---|---|---|---|---|---|---|---|---|---|---|
| S.No | MEASUREMENT STATUS | PATIENT ID | TESTING FIELD | PHOTOMETER ORDER NUMBER | BLOOD COAGULATION TIME MEASUREMENT UNIT ORDER NUMBER | MEASUREMENT SEQUENCE | PHOTOMETER | BLOOD COAGULATION TIME MEASUREMENT UNIT | SCHEDULED STATUS | MEASUREMENT STARTING TIME DIFFERENCE |
| 1 | MEASURED | 00001 | BLOOD COAGULATION | 0 | 3 | 1 | — | 10:00:00 | | |
| 2 | MEASURED | 00003 | BLOOD COAGULATION | 0 | 3 | 2 | — | 10:00:30 | | |
| 3 | MEASURED | 00005 | BLOOD COAGULATION | 0 | 3 | 3 | — | 10:05:00 | | |
| 4 | MEASURED | 00006 | BLOOD COAGULATION | 0 | 3 | 4 | — | 10:05:30 | | |
| 5 | MEASURED | 00010 | BLOOD COAGULATION | 0 | 3 | 5 | — | 10:10:00 | | |
| 6 | MEASURED | 00001 | BIOCHEMICAL | 18 | 0 | 6 | 10:10:30 | — | | 0:10:00 |
| 7 | MEASURED | 00002 | BIOCHEMICAL | 18 | 0 | 7 | 10:13:30 | — | | |
| 8 | MEASURED | 00003 | BIOCHEMICAL | 18 | 0 | 8 | 10:16:30 | — | | 0:16:30 |
| 9 | MEASURED | 00004 | BIOCHEMICAL | 18 | 0 | 9 | 10:19:30 | — | | |
| 10 | MEASURED | 00005 | BIOCHEMICAL | 18 | 0 | 10 | 10:22:30 | — | | 0:17:30 |
| 11 | MEASURED | 00007 | BIOCHEMICAL | 18 | 0 | 11 | 10:25:30 | — | | |
| 12 | MEASURED | 00008 | BIOCHEMICAL | 18 | 0 | 12 | 10:28:30 | — | | |
| 13 | MEASURED | 00009 | BIOCHEMICAL | 18 | 0 | 13 | 10:31:30 | — | | |
| 14 | MEASURED | 00010 | BIOCHEMICAL | 18 | 0 | 14 | 10:34:30 | — | | 0:24:30 |
| 15 | MEASURED | 00011 | BIOCHEMICAL | 18 | 0 | 15 | 10:37:30 | — | | |
| 16 | MEASURED | 00012 | BIOCHEMICAL | 18 | 0 | 16 | 10:40:30 | — | | |
| 17 | MEASURED | 00013 | BIOCHEMICAL | 18 | 0 | 17 | 10:43:30 | — | | |
| 18 | MEASURED | 00014 | BIOCHEMICAL | 18 | 0 | 18 | 10:46:30 | — | | |
| 19 | MEASURED | 00015 | BIOCHEMICAL | 18 | 0 | 19 | 10:49:30 | — | | |
| 20 | MEASURED | 00016 | BIOCHEMICAL | 18 | 0 | 20 | 10:52:30 | — | | |

[Fig. 8A]

MEASUREMENT SAMPLE PROGRESS LIST 801

| S. No | MEASUREMENT STATUS | PATIENT ID | TESTING FIELD | PHOTOMETER ORDER NUMBER | BLOOD COAGULATION TIME MEASUREMENT UNIT ORDER NUMBER |
|---|---|---|---|---|---|
| 1 | | 00001 | BLOOD COAGULATION | 0 | 3 |
| 2 | | 00002 | BLOOD COAGULATION | 0 | 3 |
| 3 | | 00003 | BLOOD COAGULATION | 0 | 3 |
| 4 | | 00004 | BLOOD COAGULATION | 0 | 3 |
| 5 | | 00005 | BLOOD COAGULATION | 0 | 3 |
| 6 | | 00008 | BLOOD COAGULATION | 0 | 3 |
| 7 | | 00009 | BLOOD COAGULATION | 0 | 3 |
| 8 | | 00010 | BLOOD COAGULATION | 0 | 3 |
| 9 | | 00013 | BLOOD COAGULATION | 0 | 3 |
| 10 | | 00015 | BLOOD COAGULATION | 0 | 3 |
| 11 | | 00001 | BIOCHEMICAL | 18 | 0 |
| 12 | | 00005 | BIOCHEMICAL | 18 | 0 |
| 13 | | 00006 | BIOCHEMICAL | 18 | 0 |
| 14 | | 00007 | BIOCHEMICAL | 18 | 0 |
| 15 | | 00008 | BIOCHEMICAL | 18 | 0 |
| 16 | | 00009 | BIOCHEMICAL | 18 | 0 |
| 17 | | 00010 | BIOCHEMICAL | 18 | 0 |
| 18 | | 00011 | BIOCHEMICAL | 18 | 0 |
| 19 | | 00012 | BIOCHEMICAL | 18 | 0 |
| 20 | | 00014 | BIOCHEMICAL | 18 | 0 |

[Fig. 8B]

| S. No | MEASUREMENT STATUS | PATIENT ID | TESTING FIELD | PHOTOMETER REQUEST NUMBER | BLOOD COAGULATION TIME MEASUREMENT UNIT REQUEST NUMBER | MEASUREMENT SEQUENCE | PHOTOMETER | BLOOD COAGULATION TIME MEASUREMENT UNIT | SCHEDULED STATUS |
|---|---|---|---|---|---|---|---|---|---|
| 1 | BEING ANALYZED | 0001 | BLOOD COAGULATION | 0 | 3 | 1 | — | 10:00:00 | |
| 2 | BEING ANALYZED | 0002 | BLOOD COAGULATION | 0 | 3 | 2 | — | 10:00:30 | |
| 3 | RECEIVED | 0003 | BLOOD COAGULATION | 0 | 3 | NOT DETERMINED | — | NOT DETERMINED | SCHEDULED 1 |
| 4 | RECEIVED | 0004 | BLOOD COAGULATION | 0 | 3 | NOT DETERMINED | — | NOT DETERMINED | SCHEDULED 2 |
| 5 | RECEIVED | 0005 | BLOOD COAGULATION | 0 | 3 | NOT DETERMINED | — | NOT DETERMINED | SCHEDULED 3 |
| 6 | RECEIVED | 0008 | BLOOD COAGULATION | 0 | 3 | NOT DETERMINED | — | NOT DETERMINED | SCHEDULED 4 |
| 7 | RECEIVED | 0009 | BLOOD COAGULATION | 0 | 3 | NOT DETERMINED | — | NOT DETERMINED | SCHEDULED 5 |
| 8 | RECEIVED | 00010 | BLOOD COAGULATION | 0 | 3 | NOT DETERMINED | — | NOT DETERMINED | SCHEDULED 6 |
| 9 | RECEIVED | 00013 | BLOOD COAGULATION | 0 | 3 | NOT DETERMINED | — | NOT DETERMINED | SCHEDULED 7 |
| 10 | RECEIVED | 00015 | BLOOD COAGULATION | 0 | 3 | NOT DETERMINED | — | NOT DETERMINED | SCHEDULED 8 |
| 11 | BEING ANALYZED | 00001 | BIOCHEMICAL | 18 | 18 | 3 | 10:01:00 | — | |
| 12 | RECEIVED | 00005 | BIOCHEMICAL | 18 | 18 | NOT DETERMINED | — | — | SCHEDULED 3' |
| 13 | BEING ANALYZED | 00006 | BIOCHEMICAL | 18 | 18 | 4 | 10:03:00 | — | |
| 14 | | 00007 | BIOCHEMICAL | 18 | 18 | | | | |
| 15 | | 00008 | BIOCHEMICAL | 18 | 18 | | | | |
| 16 | | 00009 | BIOCHEMICAL | 18 | 18 | | | | |
| 17 | | 00010 | BIOCHEMICAL | 18 | 18 | | | | |
| 18 | | 00011 | BIOCHEMICAL | 18 | 18 | | | | |
| 19 | | 00012 | BIOCHEMICAL | 18 | 18 | | | | |
| 20 | | 00014 | BIOCHEMICAL | 18 | 18 | | | | |

MEASUREMENT SAMPLE PROGRESS LIST / SAMPLE MEASUREMENT WAITLIST / SCHEDULED SAMPLE LIST  802

[Fig. 8C]

| S.No | S.No | PATIENT ID | TESTING FIELD | ANALYSIS ITEM NUMBER AT EACH UNIT | | MEASUREMENT SEQUENCE | PHOTOMETER SCHEDULED TIME | BLOOD COAGULATION TIME MEASUREMENT UNIT SCHEDULED TIME | SCHEDULED STATUS | MEASUREMENT STARTING TIME DIFFERENCE |
|---|---|---|---|---|---|---|---|---|---|---|
| | | | | PHOTOMETER | BLOOD COAGULATION TIME MEASUREMENT UNIT | | | | | |
| 1 | MEASURED | 00001 | BLOOD COAGULATION | 0 | 3 | 1 | - | 10:00:00 | | |
| 2 | MEASURED | 00002 | BLOOD COAGULATION | 0 | 3 | 2 | - | 10:00:30 | | |
| 3 | MEASURED | 00003 | BLOOD COAGULATION | 0 | 3 | 5 | - | 10:06:00 | | |
| 4 | MEASURED | 00004 | BLOOD COAGULATION | 0 | 3 | 6 | - | 10:06:30 | | |
| 5 | MEASURED | 00005 | BLOOD COAGULATION | 0 | 3 | 9 | - | 10:13:00 | | |
| 6 | MEASURED | 00006 | BLOOD COAGULATION | 0 | 3 | 11 | - | 10:16:30 | | |
| 7 | MEASURED | 00009 | BLOOD COAGULATION | 0 | 3 | 13 | - | 10:20:00 | | |
| 8 | MEASURED | 00010 | BLOOD COAGULATION | 0 | 3 | 15 | - | 10:23:30 | | |
| 9 | MEASURED | 00013 | BLOOD COAGULATION | 0 | 3 | 17 | - | 10:27:00 | | |
| 10 | MEASURED | 00015 | BLOOD COAGULATION | 0 | 3 | 19 | - | 10:30:30 | | |
| 11 | MEASURED | 00001 | BIOCHEMICAL | 18 | 0 | 3 | 10:01:00 | - | 0:01:00 | 0:01:00 |
| 12 | MEASURED | 00005 | BIOCHEMICAL | 18 | 0 | 10 | 10:13:30 | - | 0:00:30 | 0:00:30 |
| 13 | MEASURED | 00006 | BIOCHEMICAL | 18 | 0 | 4 | 10:03:00 | - | | |
| 14 | MEASURED | 00007 | BIOCHEMICAL | 18 | 0 | 7 | 10:07:00 | - | | |
| 15 | MEASURED | 00008 | BIOCHEMICAL | 18 | 0 | 12 | 10:17:00 | - | 0:00:30 | 0:00:30 |
| 16 | MEASURED | 00009 | BIOCHEMICAL | 18 | 0 | 14 | 10:20:30 | - | 0:00:30 | 0:00:30 |
| 17 | MEASURED | 00010 | BIOCHEMICAL | 18 | 0 | 16 | 10:24:00 | - | 0:00:30 | 0:00:30 |
| 18 | MEASURED | 00011 | BIOCHEMICAL | 18 | 0 | 8 | 10:10:00 | - | | |
| 19 | MEASURED | 00012 | BIOCHEMICAL | 18 | 0 | 18 | 10:27:30 | - | | |
| 20 | MEASURED | 00014 | BIOCHEMICAL | 18 | 0 | 20 | 10:31:00 | - | | |

| S.No | S.No | PATIENT ID | TESTING FIELD | ANALYSIS ITEM NUMBER AT EACH UNIT - PHOTOMETER | ANALYSIS ITEM NUMBER AT EACH UNIT - BLOOD COAGULATION TIME MEASUREMENT UNIT | MEASUREMENT SEQUENCE | PHOTOMETER SCHEDULED TIME | BLOOD COAGULATION TIME MEASUREMENT UNIT SCHEDULED TIME | SCHEDULED STATUS | MEASUREMENT STARTING TIME DIFFERENCE |
|---|---|---|---|---|---|---|---|---|---|---|
| 1 | MEASURED | 00001 | BLOOD COAGULATION | 0 | 3 | 1 | | 10:00:00 | | |
| 2 | MEASURED | 00002 | BLOOD COAGULATION | 0 | 3 | 2 | | 10:00:30 | | |
| 3 | MEASURED | 00003 | BLOOD COAGULATION | 0 | 3 | 3 | | 10:05:00 | | |
| 4 | MEASURED | 00004 | BLOOD COAGULATION | 0 | 3 | 4 | | 10:05:30 | | |
| 5 | MEASURED | 00005 | BLOOD COAGULATION | 0 | 3 | 5 | | 10:10:30 | | |
| 6 | MEASURED | 00008 | BLOOD COAGULATION | 0 | 3 | 6 | | 10:11:00 | | |
| 7 | MEASURED | 00009 | BLOOD COAGULATION | 0 | 3 | 7 | | 10:15:30 | | |
| 8 | MEASURED | 00010 | BLOOD COAGULATION | 0 | 3 | 8 | | 10:16:00 | | |
| 9 | MEASURED | 00013 | BLOOD COAGULATION | 0 | 3 | 9 | | 10:20:30 | | |
| 10 | MEASURED | 00015 | BLOOD COAGULATION | 0 | 3 | 10 | | 10:21:00 | | |
| 11 | MEASURED | 00001 | BIOCHEMICAL | 18 | 0 | 11 | 10:21:30 | | | 0:21:30 |
| 12 | MEASURED | 00005 | BIOCHEMICAL | 18 | 0 | 12 | 10:24:30 | | | 0:14:00 |
| 13 | MEASURED | 00006 | BIOCHEMICAL | 18 | 0 | 13 | 10:27:30 | | | |
| 14 | MEASURED | 00007 | BIOCHEMICAL | 18 | 0 | 14 | 10:30:30 | | | |
| 15 | MEASURED | 00008 | BIOCHEMICAL | 18 | 0 | 15 | 10:33:30 | | | 0:22:30 |
| 16 | MEASURED | 00009 | BIOCHEMICAL | 18 | 0 | 16 | 10:36:30 | | | 0:21:30 |
| 17 | MEASURED | 00010 | BIOCHEMICAL | 18 | 0 | 17 | 10:39:30 | | | 0:19:30 |
| 18 | MEASURED | 00011 | BIOCHEMICAL | 18 | 0 | 18 | 10:42:30 | | | |
| 19 | MEASURED | 00012 | BIOCHEMICAL | 18 | 0 | 19 | 10:45:30 | | | |
| 20 | MEASURED | 00014 | BIOCHEMICAL | 18 | 0 | 20 | 10:48:30 | | | |

804

[Fig. 9]
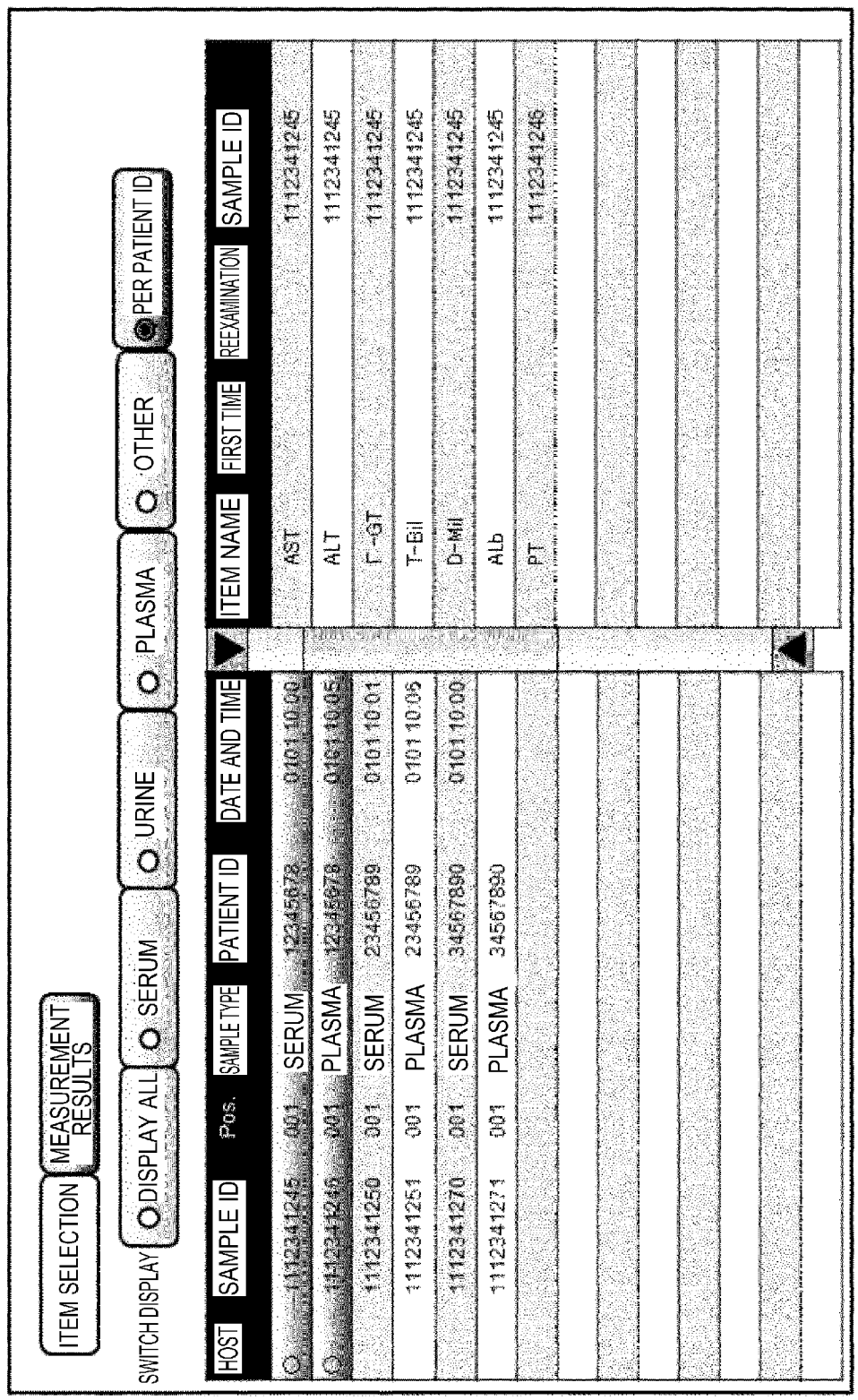

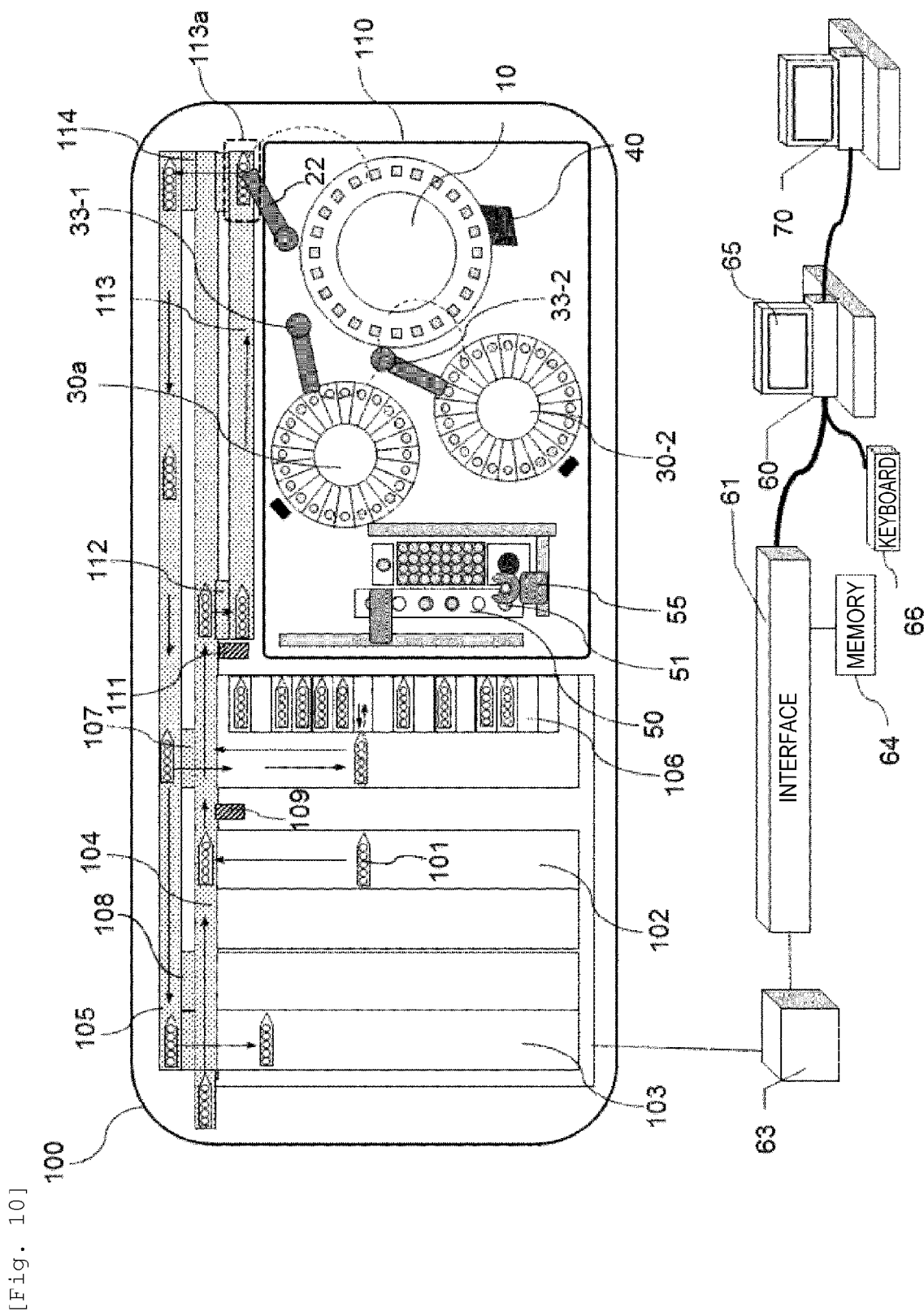
[Fig. 10]

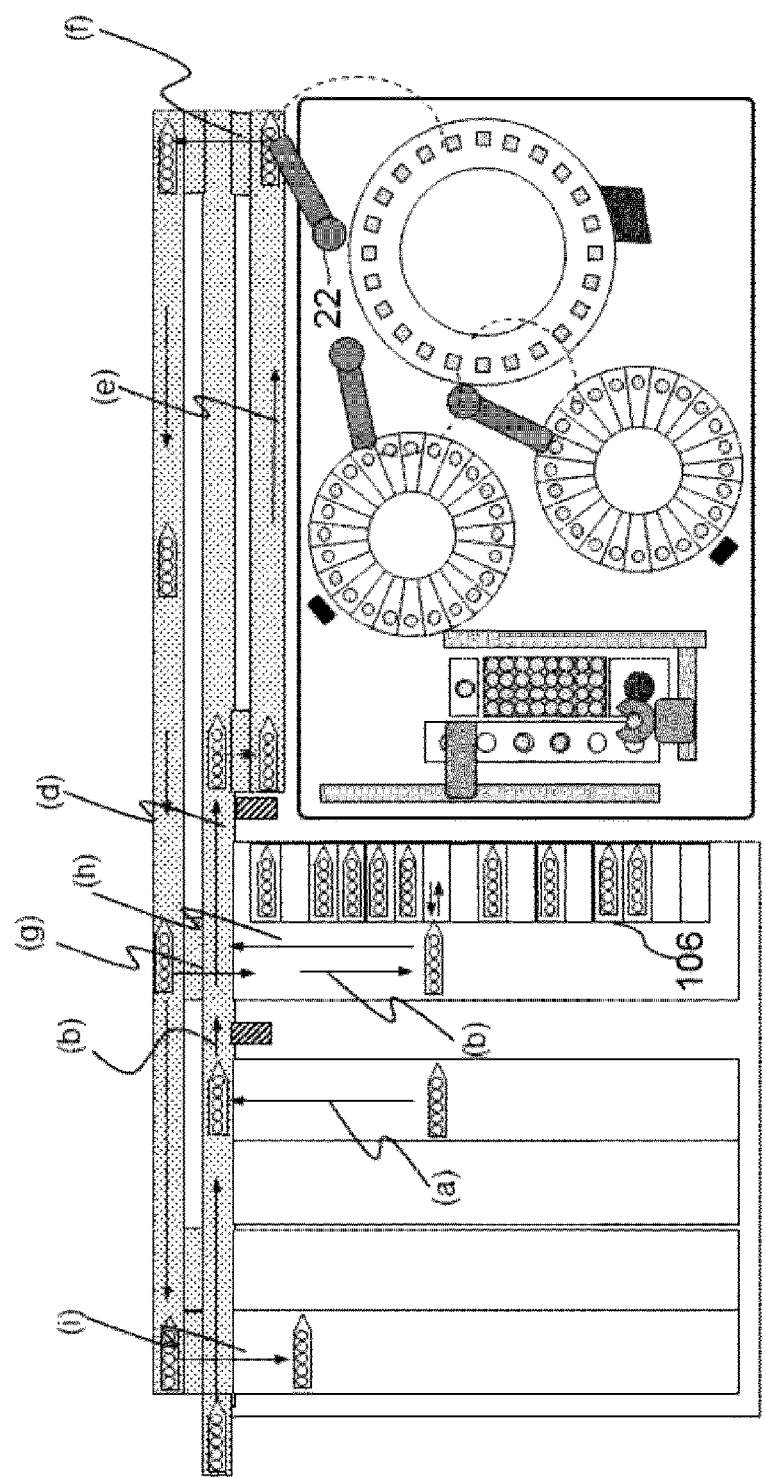
[Fig. 11]

[Fig. 12]

| SAMPLE TYPE | SERUM ▶ | PATIENT ID | 12345678 | | |
|---|---|---|---|---|---|
| SAMPLE IDENTIFICATION | ● GENERAL SAMPLE | DISC NUMBER | POSITION | SAMPLE CUP | TESTING FIELD |
| | ○ GENERAL SAMPLE | 01 | 55 | STANDARD ▶ | BIOCHEMICAL/ IMMUNOLOGICAL ▶ |

| BIOCHEMICAL 1 | BIOCHEMICAL 2 | BIOCHEMICAL 3 | IMMUNOLOGICAL | COAGULATION | Sheet 6 |
|---|---|---|---|---|---|
| AST | ALT | ALP | Γ-GT | T-cho | TG |
| TP | LD | AMY | | IP | |
| Ca | Mg | Fe | | | ISE  S.IND |

[Fig. 13]

| No. | PATIENT ID | TESTING FIELD | MEASUREMENT UNIT |
|---|---|---|---|
| 1 | 0003 | BIOCHEMICAL | PHOTOMETER |
| 2 | 0005 | BLOOD COAGULATION | PHOTOMETER |
| 3 | 0008 | BLOOD COAGULATION | PHOTOMETER |
| 4 | 0010 | BLOOD COAGULATION | BLOOD COAGULATION TIME MEASUREMENT UNIT |
| 5 | ... | ... | ... |

[Fig. 14]

| No | MEASUREMENT STATUS | SAMPLE ID | TEST ID | TESTING FIELD | MEASUREMENT SEQUENCE |
|---|---|---|---|---|---|
| 1 | MEASURED | S00001 | 030310001 | COAGULATION | - |
| 2 | MEASURED | S00002 | 030310003 | COAGULATION | - |
| 3 | MEASURED | S00003 | 030310005 | COAGULATION | - |
| 4 | MEASURED | S00004 | 030310010 | COAGULATION | - |
| 5 | MEASURED | S00005 | 030310018 | COAGULATION | - |
| 6 | MEASURED | S00006 | 030310019 | COAGULATION | - |
| 7 | MEASURED | S00007 | 030310033 | COAGULATION | - |
| 8 | MEASURED | S00008 | 030310040 | COAGULATION | - |
| 9 | BEING RECEIVED | S00009 | 030310001 | BIOCHEMICAL | 1 |
| 10 | BEING RECEIVED | S00010 | 030310002 | BIOCHEMICAL | 6 |
| 11 | BEING RECEIVED | S00011 | 030310003 | BIOCHEMICAL | 2 |
| 12 | BEING RECEIVED | S00012 | 030310004 | BIOCHEMICAL | 7 |
| 13 | BEING RECEIVED | S00013 | 030310005 | BIOCHEMICAL | 3 |
| 14 | BEING RECEIVED | S00014 | 030310007 | BIOCHEMICAL | 8 |
| 15 | BEING RECEIVED | S00015 | 030310008 | BIOCHEMICAL | 9 |
| 16 | BEING RECEIVED | S00016 | 030310009 | BIOCHEMICAL | 10 |
| 17 | BEING RECEIVED | S00017 | 030310010 | BIOCHEMICAL | 11 |
| 18 | BEING RECEIVED | S00018 | 030310011 | BIOCHEMICAL | 12 |
| 19 | BEING RECEIVED | S00019 | 030310012 | BIOCHEMICAL | 13 |
| 20 | BEING RECEIVED | S00020 | 030310013 | BIOCHEMICAL | 14 |
| 21 | BEING RECEIVED | S00021 | 030310014 | BIOCHEMICAL | 15 |
| 22 | BEING RECEIVED | S00022 | 030310015 | BIOCHEMICAL | 16 |
| 23 | BEING RECEIVED | S00023 | 030310016 | BIOCHEMICAL | 17 |
| 24 | BEING RECEIVED | S00024 | 030310017 | BIOCHEMICAL | 18 |
| 25 | BEING RECEIVED | S00025 | 030310018 | BIOCHEMICAL | 5 |

1401

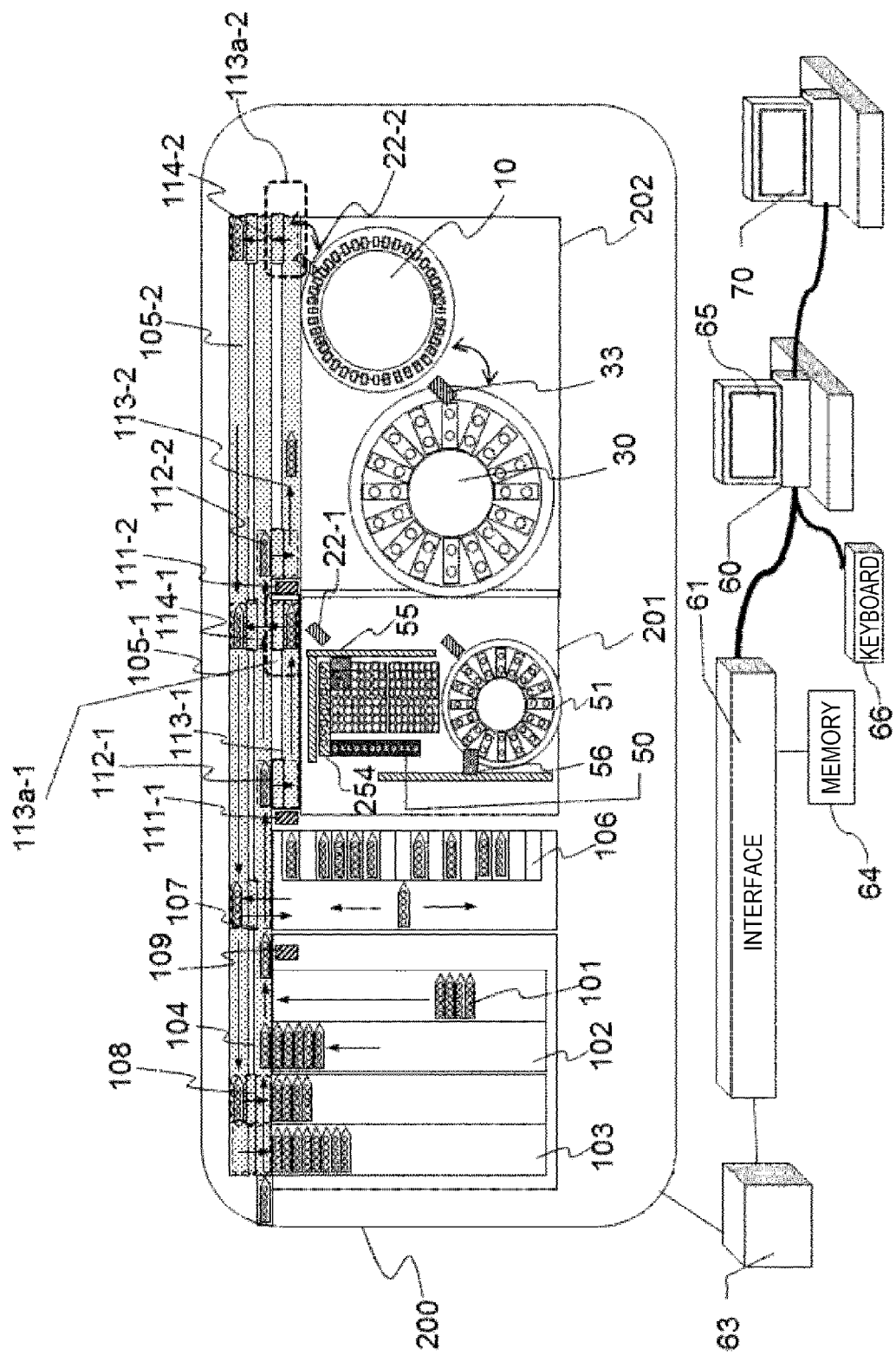
[Fig. 15]

AUTOMATED ANALYSIS DEVICE

TECHNICAL FIELD

The present invention relates to an automated analysis device for analyzing component amounts contained in samples such as blood and urine, in particular, an automated analysis device capable of measuring a first measurement item including a biochemical analysis item and a second measurement item including a blood coagulation time item (a hemostatic function testing item).

BACKGROUND ART

Sample tests that handle samples of blood, urine and the like collected from patients are classified into multiple testing fields such as a biochemical test, an immunological test and a blood coagulation test, and these multiple test results are integrated to confirm diagnosis and treatment effects.

For example, as tests for analyzing components such as blood and urine, a biochemical test that causes a reagent to react with a sample and measures components such as saccharide, lipids, proteins and enzymes, and an immunological test that measures antibodies produced when bacteria or virus enters the body, hormones, tumor markers and the like by an antigen-antibody reaction are known. Generally, the biochemical test is performed by using a biochemical automated analysis device which mixes a sample and a reagent and measures a change in color due to the chemical reaction by transmitted light, and the immunological test is performed by using an immunological testing device which, after adding antibodies in which a light emitter is bound to an antigen contained in a sample to cause an antigen-antibody reaction and washing the unbound antibodies, measures the light emission amount due to the bound antibodies. However, with the development of measurement instruments and measurement reagents in recent years, it has become possible to measure with high sensitivity due to transmitted light or scattered light using measurement methods such as immunoturbidimetry and a latex flocculation method even in a biochemical automated analysis device, and it has become possible to measure part of tumor markers, hormones and the like. Therefore, there are cases where it is possible to deal with testing items in which separate devices were conventionally required by a single device, and the difference between the two has become smaller.

In addition, in the blood coagulation test, there are tests for measuring blood coagulation time (hereinafter simply referred to as hemostatic function test, blood coagulation time measurement, etc.), which are a test of blood coagulation fibrinolytic markers for measuring control factors of blood coagulation reaction such as ATIII, enzymes working at the stage of fibrinolysis such as PIC, byproducts due to fibrinolysis such as D-dimer and FDP, and a test of hemostatic function such as PT, APTT and fibrinogen by activating the blood coagulation factors contained in the sample to proceed the blood coagulation reaction and measuring the precipitated fibrin.

In the former test of the blood coagulation fibrinolytic markers, a sample and a reagent are reacted and a change in the color due to the chemical reaction is measured, and thus a measurement with a biochemical automated analysis device is possible. In the latter hemostatic function test, it is necessary to measure the blood coagulation time and the detection method is different, and thus a dedicated blood coagulation automated analysis device is necessary.

In the hemostatic function test, it is known an automated analysis device using a method of optically measuring a change in turbidity accompanying the precipitation of fibrin and a method of physically measuring a change in viscosity accompanying the precipitation of fibrin. In recent years, in order to respond to the request for consistently measuring samples of the same patient and reporting the results, a blood coagulation analysis device in which a photometer measuring blood coagulation fibrinolytic markers and a blood coagulation time measurement unit measuring hemostatic testing items are mounted on one device has been generally known.

CITATION LIST

Patent Literature

[PTL 1] JP-A-7-49346

SUMMARY OF INVENTION

Technical Problem

In the aforementioned tests, the types of usable samples vary depending on the testing field. For example, serum or heparin sodium plasma is generally used for biochemical tests and immunological tests and citrated plasma is used in a blood coagulation testing device, and thus blood is collected being divided into blood collection tubes according to purposes at the time of blood collection and the measurement is performed using different testing devices for each measurement field. Since the samples conveyed to different devices cannot grasp the measurement state of each other, there has been a problem that, when a measurement at a device stalls, then the results are not completely available for the patient even though measurements with other testing devices have been completed and the report to the clinician side is delayed.

Patent Literature 1 discloses a method for integrally displaying, printing and transmitting analysis results of urine sediment components and urine biochemical components of urine of the same patient without newly using a computer with external urine sediment testing device and urine biochemical analysis device. However, since the measurement states of different samples are not grasped in this method, when a measurement at a device stalls, then the measurement results are not completely available for the patient even though measurements at the other testing device have been completed. As a result, the problem that the measurement results cannot be reported to the clinician side has not been solved.

Solution to Problem

As an aspect for solving the aforementioned problem, provided are an automated analysis device, and an automated analysis system and an analysis method using the device, the automated analysis device comprising a reaction cell containing a mixed solution of a sample and a reagent, a reaction disc retaining a plurality of the reaction cells on a circumference, a first measurement unit including a light source which irradiates the mixed solution contained in the reaction cells with light and a light-receiving unit which detects the irradiated light, disposable reaction containers containing a mixed solution of a sample and a reagent, a second measurement unit which has a plurality of measurement channels that retain the disposable reaction containers, and includes a light source which irradiates the disposable reaction containers retained in each of the plurality of measurement channels with light and a light-receiving unit which detects the irradiated light, a read unit which reads identification information appended to a sample container containing a sample, and a control unit which controls an analysis condition for the sample on the basis of the information that has been read, wherein the control unit has a measurement management unit which determines, for a plurality of samples having identification information that indicates the same patient, a measurement sequence for the plurality of samples on the basis of the identification information of the plurality of samples that has been read by the read unit such that a timing at which a measurement is to be performed by the first measurement unit and a timing at which a measurement is to be performed by the second measurement unit are within a predetermined period of time.

Advantageous Effects of Invention

According to the above aspect, it is possible to promptly report measurement results of each patient. Problems, configurations and effects other than those described above will be clarified by the following description of embodiments.

BRIEF DESCRIPTION OF DRAWINGS

FIG. 1 is a diagram showing a basic configuration of an automated analysis device including a biochemical analysis unit (first measurement unit) of a turntable form and a blood coagulation time analysis unit (second measurement unit) according to the present embodiment.

FIG. 2 is a diagram showing an example of a sample container installed in the automated analysis device according to the embodiment.

FIG. 3 is a flowchart showing an operation procedure of sample recognition in the automated analysis system according to the embodiment.

FIG. 4 is a diagram showing a basic configuration of a control computer of the automated analysis device according to the embodiment.

FIG. 5 is a flowchart showing an operation procedure of analysis sequence determination in the automated analysis device according to the embodiment.

FIG. 6 is a flowchart showing an operation procedure of analysis sequence determination for samples stored in a scheduled sample list in the automated analysis device according to the embodiment.

FIG. 7A is a diagram showing an example of an analysis plan according to the embodiment.

FIG. 7B is a diagram showing an example of an analysis plan according to the embodiment.

FIG. 7C is a diagram showing an example of an analysis plan according to the embodiment.

FIG. 7D is a diagram showing an example of an analysis plan according to the embodiment.

FIG. 8A is a diagram showing another example of an analysis plan according to the embodiment.

FIG. 8B is a diagram showing another example of an analysis plan according to the embodiment.

FIG. 8C is a diagram showing another example of an analysis plan according to the embodiment.

FIG. 8D is a diagram showing another example of an analysis plan according to the embodiment.

FIG. 9 is a diagram showing an example of analysis result display according to the embodiment.

FIG. 10 is a diagram showing a basic configuration of a rack type automated analysis device including a biochemical analysis unit of a turntable form and a blood coagulation time measurement unit according to an embodiment (a second embodiment).

FIG. 11 is a diagram showing a flow of sample supply in the rack type automated analysis device according to the embodiment.

FIG. 12 is a diagram showing an example of a measurement order screen according to an embodiment (a third embodiment).

FIG. 13 is a diagram showing an example of a measurement waitlist according to the embodiment.

FIG. 14 is a diagram showing an example of an analysis plan when additional orders are made subsequent to measured samples according to the embodiment.

FIG. 15 is a diagram showing a basic configuration of a module type automated analysis device including a biochemical analysis unit of a turntable form and a blood coagulation time measurement unit according to an embodiment (a fourth embodiment).

DESCRIPTION OF EMBODIMENTS

First Embodiment

The configuration and operation of the automated analysis device according to the present embodiment will be described in detail below with reference to the drawings. Throughout the drawings, the same reference numerals are attached to constituent parts having the same function in each drawing in principle, and the explanation may be omitted in some cases.

<Overall Configuration of the Device>

FIG. 1 shows a basic configuration of the automated analysis device according to the embodiment. Here, as an embodiment of the automated analysis device, an example of a composite type automated analysis device which performs biochemical analysis and blood coagulation analysis (blood coagulation fibrinolytic markers, blood coagulation time measurement) will be described.

As shown in FIG. 1, an automated analysis device 1 mainly includes a reaction disc 10, a sample disc 20, a first reagent disc 30-1, a second reagent disc 30-2, a photometer 40, a blood coagulation time measurement unit 50, a computer 60, etc.

The reaction disc 10 serving as a reaction container retaining unit is a disc-shaped unit which can rotate intermittently in the left-right direction, and a plurality of reaction cells 11 made with a translucent material can be arranged on the reaction disc 10 in the circumferential direction. The reaction cells 11 are maintained at a predetermined temperature (for example, 37° C.) by a thermostatic chamber 12.

On the sample disc 20 serving as a sample container retaining unit, a plurality of sample containers 21 containing biological samples such as blood and urine can be arranged in the circumferential direction for each of the inner and the outer two circles in the example of configuration shown in the drawing.

A sample dispensing mechanism 22 is arranged in the vicinity of the sample disc 20. The sample dispensing mechanism 22 sucks a predetermined amount of sample from the sample container 21 positioned at a dispensing (suction) position on the sample disc 20 and discharges the sample into the reaction cell 11 positioned at a dispensing (discharge) position on the reaction disc 10.

On the first reagent disc 30-1 and the second reagent disc 30-2 serving as reagent container retaining units, a plurality of first reagent bottles 31-1 and the second reagent bottles 31-2 to which labels indicating reagent identification information are affixed are arranged in the circumferential direction of the first reagent disc 30-1 and the second reagent disc 30-2 respectively. The reagent identification information includes a barcode, an RFID and the like, and here description will be made to a case where a barcode is used as an example. The first reagent bottles 31-1 and the second reagent bottles 31-2 contain reagent solutions corresponding to analysis items to be analyzed by the automated analysis device 1.

A first reagent barcode reading device 32-1 and a second reagent barcode reading device 32-2 read the reagent barcodes attached to the outer walls of the first reagent bottles 31-1 and the second reagent bottles 31-2 at the time of reagent registration. The read reagent information is registered in a memory 64 together with information on positions on the first reagent disc 30-1 and the second reagent disc 30-2. In addition, a first reagent dispensing mechanism 33-1 and a second reagent dispensing mechanism 33-2 are arranged in the vicinity of the first reagent disc 30-1 and the second reagent disc 30-2 respectively. At the time of dispensing reagent, by pipette nozzles provided in the first reagent dispensing mechanism 33-1 and the second reagent dispensing mechanism 33-2, reagents are sucked from the first reagent bottle 31-1 and the second reagent bottle 31-2 positioned at dispensing (suction) positions 30-1a and 30-2a respectively on the first reagent disc 30-1 and the second reagent disc 30-2 corresponding to the testing items and are discharged into the corresponding reaction cells 11 positioned at each of the dispensing (discharge) positions 10b and 10c on the reaction disc 10. The reaction disc 10 is stored in the thermostatic chamber 12 and is kept at a constant temperature of about 37° C.

Here, the photometer 40 is arranged on the outer peripheral side of the reaction disc 10. The light irradiated from a light source 41 arranged in the vicinity of the central portion on the inner peripheral side of the reaction disc 10 is measured by passing through the reaction cells 11 and being received by the photometer 40. In this way, a measurement unit including the photometer 40 and the light source 41 which are arranged to face each other with the reaction disc 10 in between is as a first measurement unit.

Each reaction cell 11 containing a reaction solution which is a mixed solution of a sample and a reagent is photometered every time it crosses the front of the photometer 40 during the rotation operation of the reaction disc 10. An analog signal of scattered light measured for each sample is input to an A/D (analog/digital) converter 62. The used reaction cells 11 can be used repeatedly by cleaning the inside of the reaction cells 11 by a reaction cell cleaning mechanism 34 arranged in the vicinity of the reaction disc 10.

Next, a control system and a signal processing system in the automated analysis device 1 in FIG. 1 will be briefly described. The computer 60 is connected to the A/D converter 62 and a control computer 63 via an interface 61. The computer controls operations of each mechanism of the sample dispensing mechanism 22, the first reagent dispensing mechanism 33-1, the second reagent dispensing mechanism 33-2 and the like on the control computer 63. A photometric value converted into a digital signal by the A/D converter 62 is put into the computer 60.

The memory 64 which is a storage device is connected to the interface 61 and stores information such as reagent identification information, sample identification information, analysis parameters, analysis item request contents, calibration results and analysis results.

In the drawing, the control computer 63 is connected to each constituent part and controls the entire automated analysis device. However, it may be configured to have an independent control unit in each constituent part.

Next, the analysis operation of the first measurement items relating to blood coagulation fibrinolytic markers such as D-dimer and FDP among the biochemical test and blood coagulation test of samples in the photometer 40 of the automated analysis device 1 in FIG. 1 will be described. Analysis parameters relating to items which are analyzable by the automated analysis device 1 are input in advance by an operator via an operation screen 65 and are stored in the memory 64. In order to analyze the requested and instructed testing items on each sample, the sample dispensing mechanism 22 dispenses a predetermined amount of sample from the sample container 21 to the reaction cell 11 at the dispensing position 10 according to the analysis parameters.

The reaction cell 11 into which the sample has been dispensed is conveyed by the rotation of the reaction disc 10 and is stopped at the dispensing (reagent receiving) position 10b or 10c. The first reagent dispensing mechanism 33-1 and the second reagent dispensing mechanism 33-2 dispense a predetermined amount of reagent solution to the reaction cell 11 according to the analysis parameters of the corresponding testing items. Here, contrary to the above example, the dispensing sequence of the sample and the reagent may be that the reagent is dispensed earlier than the sample.

When the reaction cell 11 crosses the photometric position, it is photometered by the photometer 40 and is converted into a numerical value which is a signal value proportional to light amount by the A/D converter 62. Then, the converted data is put into the computer 60 via the interface 61. According to the configuration using the reaction disc 10 in a turntable form, it is possible to dispense samples continuously by the rotation operation of the disc, and thus high processing capability can be obtained.

Next, on the basis of the data of the numerical value converted into the signal value as described above and data of calibration curve measured and stored in advance by an analysis method designated for each testing item, concentration data is calculated in the computer 60 and is output to the operation screen 65.

The calculation of the concentration data may be performed in the control computer 63 instead of the computer 60.

Then, the analysis operation relating to the measurement of hemostatic function testing item, that is, the measurement of blood coagulation time, in the automated analysis device in FIG. 1 will be described. A reaction container (disposable reaction container) 52 stored in a reaction container storage unit 53 is conveyed to a sample dispensing station 54 by a reaction container conveying mechanism 55. The sample dispensing mechanism 22 sucks the sample from the sample container 21 and dispenses it into the disposable reaction container 52 conveyed to the sample dispensing station 54 as described above.

Next, the disposable reaction container 52 in which the sample has been dispensed is conveyed to a blood coagulation time measurement unit 50 by the reaction container conveying mechanism 55, and the temperature is raised to 37° C. On the other hand, the reagent cold-preserved in the first reagent disc 30-1 is sucked from the first reagent bottle 32-1 corresponding to the testing item and is discharged into the corresponding empty reaction cell 11 arranged on the reaction disc 10 by the first reagent dispensing mechanism 33-1, and the temperature is raised to about 37° C. Here, description has been made to a case where the reagent in the first reagent bottle 32-1 arranged on the first reagent disc 30-1 is used for analysis as an example. However, depending on the analysis conditions, the reagent in the second reagent bottle 32-2 arranged on the second reagent disc 30-2 may be used for measurement of blood coagulation time.

After a lapse of a predetermined time, the reagent contained in the reaction cell 11 whose temperature has been raised as described above is sucked by a reagent dispensing mechanism with reagent temperature raising function 56, and then the temperature is further raised (for example, 40° C.) in this mechanism. Here, the reaction container (disposable reaction container) 52 containing the sample whose temperature has been raised to 37° C. as described above is conveyed to a measurement channel 51 in the blood coagulation time measurement unit 50 which will be described later by the reaction container conveying mechanism 55. Thereafter, the reagent dispensing mechanism with reagent temperature raising function 56 discharges the reagent whose temperature has been raised into the reaction container (disposable reaction container) 52. The blood coagulation reaction of the sample and the reagent in the reaction container 52 starts as the reagent is discharged.

The blood coagulation time measurement unit 50 which is a second measurement unit includes a plurality of measurement channels 51 each of which includes a light source and a light-receiving unit, and the light-receiving unit collects measurement data every predetermined short measurement time interval (for example, 0.1 seconds) after the reagent is discharged as described above. The collected measurement data is converted to a numerical value proportional to the light amount by the A/D converter 62 and is then put in the computer 60 through the interface 61.

The computer 60 uses data of the converted numerical value to obtain the blood coagulation time. Then, the concentration data of a target testing item is obtained on the basis of the obtained blood coagulation time and data of calibration curve prepared and stored in advance according to the testing items, and is output to the operation screen 65 of the computer 60. In addition, the used reaction container (disposable reaction container) 52 is conveyed by the reaction container conveying mechanism 55 and is discarded in a reaction container disposal unit 57. Here, the blood coagulation time and the concentration data may also be calculated by the control computer 63.

Here in the blood coagulation time measurement unit 50, since the measurement data must be collected at a predetermined short measurement time interval (for example, 0.1 seconds) as described above, only one reaction can be analyzed for one measurement channel 51.

The blood coagulation time measurement unit 50 having six measurement channels 51 is shown in FIG. 1 as an example. When there is no vacancy in any one of the measurement channels 51, for the measurement item of blood coagulation time, the automated analysis device 1 cannot accept the next measurement and enters a standby state. Therefore, of course, it also may be configured to have more measurement channels 51 depending on the analysis conditions.

Next, identification of the samples and reception of measurement orders according to the embodiment will be described. FIG. 2 shows an example of the sample container installed in the automated analysis device according to the embodiment. As shown in the drawing, a sample identifier 24 is affixed to the sample container 21 and individual identification is possible. A barcode, an RFID and the like are used in the sample identifier 24. However, description will be made to a case of using a barcode as an example here. The sample disc 20 rotates clockwise or counterclockwise when starting analysis. Here, when each sample container 21 passes the front of a sample barcode reading device (sample barcode reader) 23 shown in FIG. 1, the sample barcode reading device 23 reads the information of the barcode which is the sample identifier 24 appended to the sample container 21. The information of the barcode which has been read is stored in the memory 64 of the computer 60 via the interface 61 and is managed as the information for individually recognizing the sample. Here, as the information of the barcode, there is an ID number of the sample. Or, it may be information of at least one of a unique identifier, blood collecting date and time, age, gender, and date of birth for each patient.

The barcode information may also be a unique identifier for each testing order. Here, the unique identifier for each testing order is an ID commonly assigned to items ordered at the same time for the same patient.

The computer 60 of the automated analysis device 1 is connected to a testing information system 70 and is included in an automated analysis system. FIG. 3 is a flowchart showing an operation procedure of sample recognition in the automated analysis system according to the embodiment.

First, in the testing information system 70, when the barcode information is received from the computer 60 of the automated analysis device 1 (step 301), it is collated with sample information which has been stored and managed in advance in the testing information system 70 (step 302). Here, the sample information stored and managed in the testing information system 70 includes sample identification information, measurement order, patient identification information, etc. which will be described later. The information can be preset on the user side, and are stored and managed by inputting the correspondence relationship between the sample identification information, the measurement order and the patient identification information.

When the information managed in the testing information system 70 matches the barcode information received from the computer 60 in step 301 as a result of collation (step 303), part of or all of the sample identification information, the measurement order and the patient identification information appended to the sample information being managed are transmitted to the computer 60 (step 304). Here, the sample identification information includes ID information uniquely determined for each sample, measurement position, etc., and the patient identification information includes, besides the ID appended to each patient, at least one of a plurality of information such as gender, age, blood collecting date and time, and date of birth for the patient. When the information managed in the testing information system 70 does not match the barcode information received from the computer 60, an error of communication abnormality is output (step 305).

Next, the determination flow of the measurement sequence in the automated analysis device 1 according to the embodiment will be described with reference to FIG. 4 and FIG. 5. FIG. 4 is a diagram showing a basic configuration of the control computer of the automated analysis device according to the embodiment. As shown in the drawing, the control computer 63 includes mechanism control units 631 (631a to 631e) controlling operations of various mechanisms, measurement management units 632 (632a to 632c) controlling measurement sequences, a measurement data management unit 633 performing data processing, and an overall control unit 630 controlling these units.

In step 304 in FIG. 3, the computer 60, which has received the measurement order of the sample and the patient information from the sample information system 70, issues a command to the control computer 63 and determines the measurement sequence in the measurement management unit 632. The measurement management unit 632 includes a measurement sample progress list 632a for grasping and managing the progress state of samples currently being measured, a sample measurement waitlist 632b for grasping and managing the measurement sequence for samples to be analyzed from next measurement onward, and a scheduled sample list 632c which grasps and manages samples that cannot be analyzed immediately, that is, samples that cannot be stored in the sample measurement waitlist, for temporarily putting these samples to standby and storing them sequentially in the measurement waitlist. The mechanism control unit 631 controls the operation of each mechanism based on the measurement sample progress list 632a. In addition, after the control computer 63 receives the measurement data from the photometer 40 or the light-receiving units in each measurement channel 51, arithmetic processing is performed in real time at the measurement management unit 632, and the obtained result of the computation is immediately reflected in the measurement sample progress list 632a.

Here, as described above, the blood coagulation test includes, similar to the biochemical analysis, a test of blood coagulation fibrinolytic markers such as D-dimer and FDP which can be measured using the photometer 40, and a test of hemostatic function such as PT, APTT and fibrinogen which are measured using the blood coagulation time measurement unit 50. In the former measurement using the photometer 40, the measurement is performed by irradiating the reaction cell 11 with light from a light source when the reaction cell 11 passes through the front of the photometer 40 due to the rotation of the reaction disc 10, and thus samples can be measured continuously without stopping the measurement by the rotation operation of the reaction disc 10. In the latter measurement, it is necessary to perform the measurement continuously at a predetermined short measurement time interval (for example, every 0.1 seconds) at the blood coagulation time measurement unit 50, and measurement may be stalled in some cases depending on the analysis conditions when the number of the measurement channels 51 is small.

In the hemostatic function testing item, that is, the blood coagulation time measurement, determination is made taking the precipitation of fibrin as an index of the completion of the blood coagulation reaction, and thus it is not that the same measurement time is assigned in advance to all the samples but it is necessary to complete the measurement promptly at the timing at which it is determined that the blood coagulation reaction is completed in order to enhance the processing capability.

In such a configuration, the actual measurement time varies depending on the samples, and thus it is difficult to predict the occupancy state of the measurement channels 51. Therefore, by monitoring the vacancy state of the measurement channels 51 and controlling the measurement sequence by the measurement management unit 632, it is possible to perform measurement efficiently without enlarging the size of the device by increasing the measurement channels 51 and without lowering the processing capability. Various methods are conceivable as a method for monitoring the vacancy state here. For example, it is possible to store and manage the analysis operations of various mechanisms by the control computer 63. To be specific, it can be seen that in the time period after the operation that the reaction container (disposable reaction container) 52 is installed in a measurement channel 51 by the reaction container conveying mechanism 55 is stored and till the operation that the reaction container 52 is discarded is stored, the corresponding measurement channel 51 is not vacant. On the other hand, it can be known that when the operation that the reaction container (disposable reaction container) 52 is conveyed and discard from the corresponding measurement channel 51 by the reaction container conveying mechanism 55 after the completion of the analysis starts, there is vacancy in this measurement channel 51.

In the above description, a configuration in which the biochemical analysis and the blood coagulation fibrinolytic markers are measured at the first measurement unit and the blood coagulation time is measured at the second measurement unit has been described. However, it is not limited thereto. For example, an immunity test besides the aforementioned tests may also be executed at the first measurement unit, and it may be applied to various modes.

FIG. 5 is a flowchart showing the operation procedure of analysis sequence determination in the automated analysis device according to the embodiment.

First, when the measurement management unit 632 receives the measurement order and the patient information from the sample information system 70 (step 501), it is determined whether the testing field is a blood coagulation testing item or not (step 502). Here, as information for determining the testing field, information that it is a blood coagulation test can be directly appended to the measurement order information, and it may also be recognized from the ordered testing items, the types of the samples (citrate plasma), etc. As described above, there is a possibility that analysis cannot be performed immediately depending on the vacancy state of the blood coagulation time measurement unit 50 in the measurement of the hemostatic function testing item, and thus the processing is executed as follows.

First, when the item for which the measurement has been ordered is a blood coagulation test, it is checked whether a blood coagulation time measurement, i.e., a hemostatic function testing item is included or not (step 503). Even if the testing field is a blood coagulation test, when a hemostatic function testing item is not included, analysis can be carried out using the photometer 40 in the first measurement unit, and thus analysis can be carried out without relying on the vacancy state of the blood coagulation time measurement unit 50. Therefore, in this case, samples can be stored in the measurement waitlist in the order in which the barcodes were read (step 505). FIG. 13 is a diagram showing an example of the measurement waitlist according to the embodiment.

When a hemostatic function testing item is included in the blood coagulation testing item for which measurement has been ordered, the vacancy state of the blood coagulation time measurement unit 50 is checked (step 504). Here, it can be stored in the measurement waitlist when there is vacancy in the blood coagulation time measurement unit 50 (step 505). However, when there is no vacancy, it has to wait until there is a measurement channel 51 available in the blood coagulation time measurement unit 50. Here, the timing at which there is a measurement channel 51 available in the blood coagulation time measurement unit 50 means the timing at which the measurement of the previous sample is completed and the used reaction container 52 is discarded to the reaction container disposal unit 57 by the reaction container conveying mechanism 55.

As described above, since the measurement is completed at the timing at which it is determined the blood coagulation reaction has been completed in the hemostatic function test, the measurement time varies depending on the samples and it is not possible to predict the timing at which the measurement of the previous sample is completed to make an analysis plan. Therefore, the sample is temporarily stored in the scheduled sample list when there is no vacancy in the measurement channels 51 (step 506).

Next, when the item for which a test has been requested is a biochemical test, the flow below is followed. First, for the same patient, when the sample for blood coagulation test (hereinafter simply referred to as the blood coagulation sample) has been measured or is awaiting a measurement (step 507, step 508), the sample for the biochemical test (hereinafter simply referred to as the biochemical sample) is waiting for measurement results and it is in a state in which a report is unavailable to the patient, and thus the sample is stored in the measurement waitlist in the order in which the barcodes were read (step 511). When the blood coagulation sample of the same patient is in the scheduled sample list (step 509), the report is unavailable to the patient until the result of the target blood coagulation sample is available even if the measurement of the biochemical sample has been completed. Therefore, the sample is scheduled on the scheduled sample list in synchronization with the target blood coagulation sample stored in the scheduled sample list (step 510). Here, synchronization means, for example, to store samples of the same patient in the scheduled sample list in a consecutive order such that the samples of the same patient are preferentially analyzed consecutively.

Next, with reference to FIG. 6, the operation procedure of the analysis sequence determination of the samples stored in the scheduled sample list in the automated analysis device according to the embodiment will be described.

That the samples are stored in the scheduled sample list means that there is no vacancy in the measurement channels 51 in the blood coagulation time measurement unit 50. Therefore, it is only necessary to determine whether the measurement of the next sample is possible at the timing of the completion of the measurement at the measurement channels 51. Even when the measurement in a measurement channel 51 has been completed (step 601), the vacancy state of other measurement channels 51 are also checked and it is determined whether the number of the vacant measurement channels is larger by comparing the number of items ordered at the top of the scheduled sample list with the number of the measurement channels on which measurement is possible (step 602). Here, when the number of the vacant measurement channels is smaller, it is not possible to carry out all the measurements of the sample, and thus the process returns to step 601 to wait until measurement of the sample measurement waitlist is completed and another measurement channel 51 is available. When the number of the vacant measurement channels on which measurement is possible is larger than the number of items ordered at the top of the scheduled sample list, the samples are inserted at the top of the sample measurement waitlist (step 604) after confirming that there is no order of another blood coagulation time item in the sample measurement waitlist (step 603). When there is an order of another blood coagulation time item in the sample measurement waitlist (step 603), the blood coagulation test of the sample measurement waitlist is prioritized, and thus the process returns to step 601 to wait until the measurement of the sample measurement waitlist is completed and the measurement channel 51 is available again.

Next, a method for creating an analysis plan for analyzing the blood coagulation samples (number of samples: 5 samples) and the biochemical samples (number of samples: 15 samples) in the automated analysis device 1 according to the embodiment which has been described with reference to FIG. 1 will be described in detail with reference to FIG. 5, FIG. 6 and FIGS. 7A-7d.

FIGS. 7A-7C show examples of the analysis plan according to the embodiment and also not according to the embodiment. For convenience of explanation, the analysis plan is simulated by assuming that the sampling interval in the automated analysis device 1 is 10 seconds and it takes 5 minutes from the sampling to the completion of the measurement at the blood coagulation time measurement unit 50, and the analysis plan is shown in 701 to 704 in FIGS. 7A-7D. 701 is a diagram showing a state before the start of the measurement in the measurement sample progress list according to the embodiment. 702 shows the measurement sample progress list and the sample measurement waitlist according to the embodiment, and includes the ones whose measurement status is "received" or "being analyzed". 703 shows the measurement sample progress list, the sample measurement waitlist and the scheduled sample list according to the embodiment, and shows modes whose measurement status is "measured". 704 shows the measurement sample progress list, the sample measurement waitlist and the scheduled sample list where the embodiment is not applied, and shows modes whose measurement status is "measured". As shown in 701, when 15 samples are ordered in total for the blood coagulation samples including a request for three items of the hemostatic function testing items and the biochemical samples including 18 items of the biochemical testing items in the measurement sample progress list, the sample barcode reading device 23 reads the information of the sample identifiers 24 affixed to the sample containers 21 and the measurement sequence is determined from sample number (hereinafter may be simply referred to as S. No.) 1 in this order. First, in S. No. 1, the testing field is a blood coagulation testing item (step 502) and includes a hemostatic function testing item (step 503). There is vacancy in the measurement channels 51 of the blood coagulation measurement unit 50 immediately after the start of the test (step 504), and thus the samples are stored in the measurement waitlist (step 505) and the analysis is started. In the case of the configuration of the automated analysis device 1 shown in FIG. 1, since the blood coagulation time measurement unit 50 has six measurement channels 51, S. No. 2 can be analyzed in the same manner.

However, at this timing (the timing of analyzing S. No. 2), there is no vacancy in the measurement channels 51 in the blood coagulation time measurement unit 50 (step 504), and thus it is not possible to determine the analysis plan for S. No. 3 to S. No. 5. Therefore, the samples are stored in the scheduled sample list (step 506).

Since the blood coagulation sample of S. No. 6 (the same patient in patient ID: 00001) has already been measured (step 507), it is stored in the measurement waitlist (step 511) and analysis is carried out (702).

By repeating the same determination and executing the analysis, it is possible to complete the sampling of all 20 samples in 44 minutes 30 seconds from the start of all the analyses as shown in 703.

As shown in 704, when the analysis is carried out in the order in which the barcodes were read, a time loss occurs due to waiting for vacancy in the measurement channels 51 of the blood coagulation time measurement unit 50 at the time of measurement of S. No. 3 and S. No. 5 and it takes 52 minutes 30 seconds to complete the sampling of all 20 samples from the start of the analysis.

Furthermore, according to the embodiment, there is also an effect of reducing the difference in measurement time (measurement timing) in the same patient. Taking the patient ID: 00010 as an example, the difference between the sampling time in the blood coagulation time measurement unit 50 and the sampling time in the photometer 40 is 12 minutes 30 seconds in 703. In contrast, this difference is 24 minutes 30 seconds in 704.

That is, by applying the embodiment, it is possible to enhance the efficiency of the entire tests and to smoothly report to the clinician side by, for the same patient for whom different types of tests are requested, performing as possible such that the measurement time (measurement timing) and the output of the measurement result are at the same time or within a predetermined period of time.

Moreover, when the number of the blood coagulation samples is large, the effect is further increased. Here, an example of analyzing the blood coagulation samples (number of samples: 10 samples) and the biochemical samples (number of samples: 10 samples) will be described with reference to FIG. 8. 801 is a diagram showing a state before the start of the measurement in the measurement sample progress list according to the embodiment. 802 shows the measurement sample progress list and the sample measurement waitlist according to the embodiment, and includes the ones whose measurement status is "received" or "being analyzed". 803 shows the measurement sample progress list, the sample measurement waitlist and the scheduled sample list according to the embodiment, and shows modes whose measurement status is "measured". 804 shows the measurement sample progress list, the sample measurement waitlist and the scheduled sample list where the embodiment is not applied, and shows modes whose measurement status is "measured".

As shown in 801, first, in S. No. 1 and S. No. 2, the testing field is a blood coagulation testing item (step 502) and includes a hemostatic function test (step 503). There is vacancy in the measurement channels 51 immediately after the start of the test (step 504), and thus the samples are stored in the measurement waitlist (step 505) and the analysis is started. At this timing (the timing of analyzing S. No. 2), there is no vacancy in the blood coagulation time measurement unit 50, and thus it is not possible to determine the analysis plan for S. No. 3 to S. No. 10. Therefore, the samples are stored in the scheduled sample list (step 506).

In S. No. 11 (patient ID: 00001), since the blood coagulation sample of the same patient has already been measured (step 507), it is stored in the measurement waitlist (step 511) and analysis is carried out (802). However, in the next S. No. 12 (patient ID: 00005), since the blood coagulation sample of the same patient is stored in the scheduled sample list (step 509), it is synchronized with the target blood coagulation sample in the scheduled sample list and is stored in the scheduled sample list (step 510).

By repeating the same determination and executing the analysis, it is possible to complete the sampling of all 20 samples in 31 minutes from the start of all the analyses as shown in 803.

On the other hand, as shown in 804, when the analysis is carried out in the order in which the barcodes were read, a time loss occurs according to the vacancy state in the measurement channels 51 of the blood coagulation time measurement unit 50 and it takes 48 minutes 30 seconds to complete the sampling of all 20 samples from the start of the analysis.

In addition, with respect to the difference in measurement time (measurement timing) in the same patient, the difference between the sampling time at the blood coagulation time measurement unit 50 and the sampling time at the photometer 40 is at most 1 minute in 803. In contrast, this difference is at most 22 minutes 30 seconds in 804.

In the above described FIGS. 7A-7D and FIG. 8, the method of determining the measurement sequence while reading the barcodes appended to the samples after starting the analysis at the same time has been described. However, the same method may also be applied to the measured samples. Furthermore, in FIGS. 7A-7D and FIG. 8, the case where the patient IDs are the same has been described as an example. However, it may also be applied to the case where the test IDs, instead of the patient IDs, are the same.

FIG. 14 is a diagram showing an example of an analysis plan when additional orders of measurement of new samples are made subsequent to measured samples according to the embodiment. Here, description will be made to a case where the new samples which have been additionally ordered are given the same test ID as the measured samples. A case where additional samples (Nos. 9 to 25) were set up after the completion of the measurement of eight samples (Nos. 1 to 8) whose testing field is blood coagulation and the measurement was started will be described in detail. For the samples of registered Nos. 9 to 25 added later, the sample IDs: S00009, S00011, S00013, S00017 and S00025 have the same test ID as the measured samples S00001, S00003, S00005, S00010 and S00018. Although the measurement has already been completed for S00001, S00003, S00005, S00010 and S00018, there is still a possibility that the measurement results cannot be reported for the patient because another testing item ordered at the same time for the same patient remains. Therefore, as shown in the drawing, analysis is planned so as to preferentially measure S00009, S00011, S00013, S00017 and S00025. The automated analysis device rotates the sample disc 20 clockwise or counter-clockwise in accordance with the determined measurement sequence, and conveys the target sample to the sample dispensing position 20a to dispense. With such a configuration, even when there is an additional order, it is possible to minimize the waiting time in reporting the measurement results to the patient.

Next, an example of analysis result display according to the embodiment will be described with reference to FIG. 9. In the automated analysis device 1 according to the embodiment, patient sample information can be managed by using the sample identifier 24 and the testing information system 70. The display of the measured results may be classified by sample type, and it is also possible to display the results of the same patient collectively. By setting the sorting and searching of results for each patient to be executable, there is an effect that an operator can check at any time the measurement status and results for each patient.

Here, an example of a patient ID is shown in FIG. 9 as the patient sample information. However, as mentioned above, a test ID may be used instead of the patient ID.

As such, by using the scheduled sample list and monitoring the vacancy state of the blood coagulation time measurement unit 50 to determine the analysis sequence, it is possible to manage the measurement sequence for each patient even if different blood collection tubes were used in the tests while preventing the increase of the size of the device. Moreover, by integrating the results of measurement according to conditions, it is possible to contribute to expediting report to clinic.

Second Embodiment

In the present embodiment, an example of application to the configuration of a composite type automated analysis device (rack type) 100 including a biochemical analysis unit of a turntable form and a blood coagulation time measurement unit will be described with reference to FIG. 10.

The main difference in configuration between the automated analysis device (rack type) 100 and the automated analysis device 1 shown in FIG. 1 in the first embodiment is that the automated analysis device 100 has, as the sample container retaining unit, a sample rack 101 instead of the sample disc 20. Here, the sample rack 101 can retain one or more sample containers. FIG. 10 shows the sample rack 101 retaining five sample containers as an example. In addition, the automated analysis device (rack type) 100 mainly includes a rack supply unit 102, a rack storage unit 103, a conveying line 104 conveying the sample rack 101 to an analysis unit 110, a return line 105 conveying the sample rack 101 in a direction contrary to the conveying line 104, a rack standby unit 106, a standby unit handling mechanism 107 which draws the sample rack 101 from the conveying line 104 and the return line 105 to the rack standby unit 106, a rack returning mechanism 108, a read unit (conveying line) 109 which reads identification information such as barcode appended to the sample rack 101 of the conveying line 104, and the analysis unit 110. Here, the descriptions overlapping with the contents described in the first embodiment are omitted, and a method of supplying samples peculiar to the configuration of the automated analysis device (rack type) 100 will be described in detail. Although a line type including the conveying line 104 and the return line 105 as the conveying unit is described here, it may also be a handling mechanism movable in both directions and it may be applied to various modes.

In the automated analysis device (rack type) 100 according to the embodiment, the conveying system of the analysis unit 110 arranged along the conveying line 104 includes a read unit (analysis unit) 111 for collating analysis request information for a sample, a rack handling mechanism (1) 112 that receives the sample rack 101 from the conveying line 104, a dispensing line 113 that can cause the sample rack 101 to standby till the start of dispensing and conveys the sample racks 101 up to a sampling area 113*a* where sample is dispensed in the sample containers of the sample rack 101, and a rack handling mechanism (2) 114 that conveys the sample rack 101 to the return line 205 after the sample dispensing.

Upon receiving an instruction to start analysis from the computer 60, the sample rack 101 arranged in the rack supply unit 102 is transferred to the conveying line 104 (FIG. 11 (*a*)). Here, individual identification media affixed to the sample rack 101 on the conveying line 104 and the sample container 21 stored in the sample rack are read by the read unit (conveying line) 109, and the sample rack number and the sample container number are recognized (FIG. 11 (*b*)).

The sample read by the read unit (conveying line) 109 is stored in the rack standby unit 106 to wait for analysis when there is a sample rack 101 on the dispensing line 113 (FIG. 11 (*c*)). The standby sample rack 101 is sent to the analysis unit 110 when the dispensing of the sample on the dispensing line 113 is completed, and the sample rack number and the sample container number are recognized at the read unit (analysis unit) 111 (FIG. 11 (*d*)). Then the sample is sent to the dispensing line 113 (FIG. 11 (*e*)) via the rack handling mechanism (1) 112, and the sample is dispensed by the sample dispensing mechanism 22. In this case, when there is no sample rack 101 on the dispensing line 113, the sample may be directly conveyed to the dispensing line 113 without being stored in the rack standby unit 106.

The dispensed sample is conveyed to the return line 105 via the rack handling mechanism (2) 114 (FIG. 11 (*f*)), and is sent to the rack standby unit 106 via the standby unit handling mechanism 107 (FIG. 11 (*g*)). In the rack standby unit 106, a plurality of sample racks 101 can be stored, and by transferring the necessary sample rack 101 to the conveying line 104 every time as the measurement sequence is replaced, it is possible to respond flexibly. When all the analyses are completed and it is determined that there is no retesting, the sample is conveyed to the rack storage unit 103 (FIG. 11 (*i*)) via the standby unit handling mechanism 107 (FIG. 11 (*h*)).

The other analysis operations and the operation procedures accompanying the replacement and the like of the measurement sequence in the case where the blood coagulation samples and the biochemical samples coexist are the same as the contents described in the first embodiment, and thus detailed description is omitted. However, as described above, the sample stored in the scheduled sample list is not measured immediately but is temporarily sent to the rack standby unit 106 to wait for the measurement, and in this way measurement can be continued without relying on the vacancy of the blood coagulation time measurement unit 50.

Third Embodiment

In the first embodiment, a method for enabling measurement progress management and display of measurement results for each patient by receiving patient information from the testing information system 70 has been described. In the present embodiment, a brief description will be made to the fact that the same processing can be performed even when the automated analysis device 1 is not connected to the testing information system 70. Since the configuration and operation of the automated analysis device 1, the control and signal processing, the determination of the measurement sequence, and the display of the results are the same as those of the first embodiment, the description thereof is omitted, and a description will be made especially to the identification of the sample and the reception of measurement order.

In the automated analysis device 1 which is not connected to the testing information system 70, an operator carries out measurement by performing an order from the operation screen 65. FIG. 12 shows an example of the measurement order screen according to the embodiment.

Samples are individually identified by selecting the installation position of the sample container in the sample disc 20 and measurement items from the request screen. At this time, alphanumeric characters that can be individually identified may be input using a keyboard 66 in the patient ID column as additional information. In this case, by inputting the same patient ID, testing field and sample types (classification of serum, plasma, etc.) to the order information of different blood collection tubes of the same patient, sample identification becomes possible in the device. Since samples can be recognized by the above method, it is possible to conduct search for the same patient ID, determine the measurement sequence, and display the measurement results collectively as described in the first embodiment.

Fourth Embodiment

In the present embodiment, an example of application to the configuration of a composite type automated analysis device (module type) 200 including a blood coagulation time measurement unit 201 and a biochemical analysis unit 202 of a turntable form will be described with reference to FIG. 15.

The main difference in configuration between the automated analysis device (module type) 200 and the automated analysis devices 1 and 100 shown in FIG. 1 and FIG. 10 in the first and the second embodiments is that a sample probe 22 is individually provided in each of the blood coagulation time measurement unit 201 and the biochemical analysis unit 202 of a turntable form. Here, the descriptions overlapping with the contents described in the first and the second embodiments are omitted, and a sample supply method peculiar to the configuration of the automated analysis device (module type) 200 and the blood coagulation time measurement unit 201 will be described in detail. Although a line type including the conveying line 104 and the return line 105 as the conveying unit is described here, and it may be applied to various conveying modes such as a handling mechanism movable in both directions.

In the automated analysis device (module type) 200 according to the embodiment, the conveying system of the analysis units (the blood coagulation time measurement unit 201, the biochemical analysis unit 202) arranged along the conveying line 104 includes read units (analysis units) 111-1 and 111-2 for collating analysis request information for samples, rack handling mechanisms (1) 112-1 and 112-2 that receive the sample rack 101 from the conveying line 104, a dispensing line 113 that can cause the sample rack 101 to standby till the start of dispensing and conveys the sample racks 101 up to sampling areas 113a-1 and 113a-2 where samples are dispensed in the sample containers of the sample racks 101, and rack handling mechanisms (2) 114-1 and 114-2 that convey the sample racks 101 to the return line 205 after the sample dispensing and are individually provided for each unit.

In this way, samples necessary for each unit of the blood coagulation time measurement unit 201 and the biochemical analysis unit 202 of a turntable form are supplied at necessary timings. Here, the sample rack 101 is shown with a structure capable of retaining a plurality of sample containers 21 as an example. However, there may also be one storable sample container 21.

The sample containers 21 conveyed to the sampling area 113a-1 in the vicinity of the blood coagulation time measurement unit 201 dispense samples to the reaction containers 52 installed in a movable sample dispensing station 254 by the sample dispensing mechanism 22-1. The movable sample dispensing station 254 is structured to be accessible by the reaction container conveying mechanism 55, and the reaction containers are conveyed from the reaction container storage unit 53 by installing empty reaction containers 52.

The reaction containers 52 into which the sample has been dispensed are conveyed to the measurement channels 51 of the blood coagulation time measurement unit 50 and are heated, and wait for dispensing of a reagent. Here, the reagent is dispensed by the reagent dispensing mechanism with reagent temperature raising function 56 and the measurement is started.

Analysis operations in the biochemical analysis unit 202 for the sample containers 21 conveyed to the sampling area 113a-2 in the vicinity of the biochemical analysis unit 202 are substantially the same as those described in the first embodiment, and thus the descriptions are omitted here.

REFERENCE SIGNS LIST

1: automated analysis device
10: reaction disc
10a: dispensing (discharging) position
11: reaction cell
12: thermostatic chamber
20: specimen disc (sample disc)
20a: dispensing (suction) position
21: sample container
22: sample dispensing mechanism
23: sample barcode reading device (sample barcode reader)
24: sample identifier
30: reagent disc
30-1: first reagent disc
30-2: second reagent disc
30-1a: dispensing (suction) position
30-2a: dispensing (suction) position
31: reagent bottle
31-1: first reagent bottle
31-2: second reagent bottle
32: reagent barcode reading device (reagent barcode reader)
32-1: first reagent barcode reading device
32-2: second reagent barcode reading device
33-1: first reagent dispensing mechanism
33-2: second reagent dispensing mechanism
40: photometer
41: light source
50: blood coagulation time measurement unit
51: measurement channel
52: reaction container (disposable reaction container)
53: reaction container storage unit
54: sample dispensing station
55: reaction container conveying mechanism
56: reagent dispensing mechanism with temperature raising function
57: reaction container disposal unit
60: computer
61: interface
62: A/D converter
63: control computer
64: memory
65: operation screen
66: keyboard
70: testing information system
100: automated analysis device (rack type)
101: sample rack
102: rack supply unit
103: rack storage unit
104: conveying line
105: return line
106: rack standby unit
107: standby unit handling mechanism
108: rack returning mechanism
109: read unit (conveying line)
110: analysis unit
111: read unit (analysis unit)
112: rack handling mechanism (1)
113: dispensing line 113a: sampling area
114: rack handling mechanism (2)
200: automated analysis device (module type)
201: blood coagulation time measurement unit
202: biochemical analysis unit
254: movable sample dispensing station

The invention claimed is:

1. An automated analysis device comprising
a sample disk configured to retain a sample container containing a sample,
a reagent disc configured to retain a reagent container containing a reagent,
a sample dispensing mechanism configured to dispense a sample,
a reagent dispensing mechanism configured to dispense a reagent,
a reaction disc configured to retain a plurality of reaction cells containing a mixed solution of the sample and the reagent on a circumference,
a first measurement unit including a light source configured to irradiate the mixed solution contained in the reaction cells with light, and a light-receiving unit which detects the irradiated light,
a second measurement unit having a plurality of measurement channels that retain disposable reaction containers containing the mixed solution of the sample and the reagent, and includes a light source which irradiates the disposable reaction containers retained in each of the plurality of measurement channels with light, and a light-receiving unit which detects the irradiated light,
a read unit configured to read identification information appended to a sample container containing a sample, and
a control unit controlling an analysis condition for the sample on the basis of the information that has been read, wherein
the control unit is configured to:
determine a measurement sequence for the samples on the basis of the identification information of the plurality of samples that has been read by the read unit,
perform processing for a plurality of samples having identification information that indicates the same patient, wherein a first sample for which a testing item that should be measured by the first measurement unit has been ordered and a second sample for which a testing item that should be measured by the second measurement unit has been ordered furthermore have the same identification information pertaining to testing, and
determine, on the basis of a timing at which the measurement for one of the first sample or the second sample is to be performed, the timing at which the measurement for the other sample of the first sample or the second sample is to be performed,
wherein the sample disk conveys the retained sample containers on the basis of the determined measurement sequence,
wherein the control unit is configured to store a measurement sample progress list for managing the progress state of samples currently being measured, a sample measurement waitlist for managing the measurement sequence for samples to be measured at a later time, and a scheduled sample list for managing samples that cannot be stored in the sample measurement waitlist because standby is necessary, and
wherein the control unit is configured to determine whether to store a sample in the sample measurement waitlist or in the scheduled sample list based on the vacancy state of the second measurement unit.

2. The automated analysis device according to claim 1, wherein
the control unit is configured to determine the measurement sequence for the samples such that the timing at which the measurement for the one of the first sample or the second sample is to be performed, and the timing at which the measurement for the other sample of the first sample or the second sample is to be performed are within a predetermined period of time.

3. The automated analysis device according to claim 1, wherein
the sample disc is configured to rotate clockwise or counterclockwise.

4. The automated analysis device according to claim 1, wherein
the sample disk includes a sample rack supply unit configured to supply a sample rack retaining one or more sample containers, a sample rack conveying unit configured to convey the supplied sample rack, a sample rack standby unit configured to cause the sample rack waiting for an analysis to standby, and a sample rack storage unit configured to store the sample rack on which the analysis has been completed.

5. The automated analysis device according to claim 1, wherein
the light source and the light-receiving unit in the first measurement unit are arranged to face each other with a reaction container retained in the reaction disc in between.

6. The automated analysis device according to claim 1, wherein
the automated analysis device includes a cleaning mechanism configured to clean the reaction cells having undergone measurement at the first measurement unit.

7. The automated analysis device according to claim 1, wherein
the first measurement unit performs analysis of at least one of biochemical test, immunological test, and blood coagulation fibrinolytic markers in blood coagulation test, and
the second measurement unit performs blood coagulation time measurement in blood coagulation test.

8. The automated analysis device according to claim 1, wherein
the identification information is appended to the sample container and is ID information or measurement position uniquely determined for each sample.

9. The automated analysis device according to claim 1, wherein
the identification information is appended to the sample container and is information of at least one of a unique identifier, blood collecting date and time, age, gender, and date of birth for each patient.

10. The automated analysis device according to claim 1, wherein
the identification information is appended to the sample container and is information of at least one of a unique identifier, blood collecting date and time, age, gender, and date of birth for each testing order.

11. The automated analysis device according to claim 1, wherein
the control unit is configured to:
cause the second sample to wait when there is no vacancy in the second measurement unit, and after detecting that there is vacancy in the second measurement unit, determine the measurement sequence for samples such that the second sample is measured at the second measurement unit.

12. The automated analysis device according to claim 1, wherein
the control unit is configured to:
temporarily store the sample in the scheduled sample list when there is no vacancy in the second measurement unit, and
after detecting that there is vacancy in the second measurement unit, store the sample stored in the scheduled sample list to the sample measurement waitlist from the scheduled sample list.

13. The automated analysis device according to claim 1, wherein
on the basis of the identification information of the sample for which a measurement at the first measurement unit has been requested, when another sample of the same patient for which a measurement at the second measurement unit has been requested is stored in the scheduled sample list, the control unit is configured to store information regarding the sample for which a measurement at the first measurement unit has been requested in the scheduled sample list in synchronization with information of the another sample.

14. The automated analysis device according to claim 1, wherein
the control unit is configured to:
display, on a display unit, measurement results classified by at least one of sample type, patient ID, and testing ID on the basis of the identification information of a plurality of samples read by the read unit.

15. An automated analysis system comprising an automated analysis device and a testing information system communicably connected to the automated analysis device, the automated analysis device comprising:
a sample container retaining unit configured to retain a sample container containing a sample,
a reagent disc configured to retain a reagent container containing a reagent,
a sample dispensing mechanism configured to dispense a sample,
a reagent dispensing mechanism configured to dispense a reagent,
a reaction disc configured to retain a plurality of reaction cells containing a mixed solution of the sample and the reagent on a circumference,
a first measurement unit including a light source configured to irradiate the mixed solution contained in the reaction cells with light, and a light-receiving unit configured to detect the irradiated light,
a cleaning mechanism configured to clean the reaction cells having undergone measurement at the first measurement unit,
disposable reaction containers containing the mixed solution of sample and reagent,
a second measurement unit having a plurality of measurement channels that retain the disposable reaction containers and includes a light source which irradiates the disposable reaction containers retained in each of the plurality of measurement channels with light, and a light-receiving unit configured to detect the irradiated light,
a read unit configured to read identification information appended to a sample container containing a sample, and
a control unit controlling an analysis condition for the sample on the basis of the information that has been read, wherein
the control unit is configured to:
determine a measurement sequence for the samples on the basis of the identification information of the plurality of samples that has been read by the read unit,
perform processing for a plurality of samples having identification information that indicates the same patient, wherein a first sample for which a testing item that should be measured by the first measurement unit has been ordered and a second sample for which a testing item that should be measured by the second measurement unit has been ordered furthermore have the same identification information pertaining to testing,
determine, on the basis of a timing at which the measurement for one of the first sample or the second sample is to be performed, the timing at which the measurement for the other sample of the first sample or the second sample is to be performed,
wherein the sample container retaining unit conveys the retained sample containers on the basis of the determined measurement sequence,
wherein the control unit is configured to store a measurement sample progress list for managing the progress state of samples currently being measured, a sample measurement waitlist for managing the measurement sequence for samples to be measured at a later time, and a scheduled sample list for managing samples that cannot be stored in the sample measurement waitlist because standby is necessary, and
wherein the control unit is configured to determine whether to store a sample in the sample measurement waitlist or in the scheduled sample list based on the vacancy state of the second measurement unit.

16. An analysis method using an automated analysis device, the automated analysis device comprising:
a sample container retaining unit configured to retain a sample container containing a sample,
a reagent disc configured to retain a reagent container containing a reagent,
a sample dispensing mechanism configured to dispense the sample,
a reagent dispensing mechanism configured to dispense the reagent,
a reaction disc configured to retain a plurality of reaction cells containing a mixed solution of the sample and the reagent on a circumference,
a first measurement unit including a light source configured to irradiate the mixed solution contained in the reaction cells with light, and a light-receiving unit configured to detect the irradiated light,
a cleaning mechanism configured to clean the reaction cells having undergone measurement at the first measurement unit,
disposable reaction containers containing the mixed solution of sample and reagent,
a second measurement unit having a plurality of measurement channels that retain the disposable reaction containers and includes a light source configured to irradiate the disposable reaction containers retained in each of the plurality of measurement channels with light, and a light-receiving unit configured to detect the irradiated light, a read unit configured to read identification information appended to a sample container containing a sample, and a control unit controlling an analysis condition for the sample on the basis of the information that has been read, wherein the control unit is configured to:

determine a measurement sequence for the samples on the basis of the identification information of the plurality of samples that has been read by the read unit, perform processing for a plurality of samples having identification information that indicates the same patient, wherein a first sample for which a testing item that should be measured by the first measurement unit has been ordered and a second sample for which a testing item that should be measured by the second measurement unit has been ordered furthermore have the same identification information pertaining to testing, and determine, on the basis of a timing at which the measurement for one of the first sample or the second sample is to be performed, the timing at which the measurement for the other sample of the first sample or the second sample is to be performed, and wherein the sample container retaining unit conveys the retained sample containers on the basis of the determined measurement sequence, wherein the control unit is configured to store a measurement sample progress list for managing the progress state of samples currently being measured, a sample measurement waitlist for managing the measurement sequence for samples to be measured at a later time, and a scheduled sample list for managing samples that cannot be stored in the sample measurement waitlist because standby is necessary, and wherein the control unit is configured to determine whether to store a sample in the sample measurement waitlist or in the scheduled sample list based on the vacancy state of the second measurement unit.

* * * * *